(12) United States Patent
Sun et al.

(10) Patent No.: US 6,391,024 B1
(45) Date of Patent: May 21, 2002

(54) RF ABLATION APPARATUS AND METHOD HAVING ELECTRODE/TISSUE CONTACT ASSESSMENT SCHEME AND ELECTROCARDIOGRAM FILTERING

(75) Inventors: Weimin Sun, Plymouth, MN (US); Thomas M. Castellano, Temecula, CA (US); Russ E. Anderson, Marine on St. Croix, MN (US); Wade A. Bowe, Temecula, CA (US); John A. Simpson, Carlsbad, CA (US); Marshall L. Sherman, Cardiff, CA (US); Kathryn E. Lockwood, San Diego, CA (US)

(73) Assignee: Cardiac Pacemakers, Inc., St. Paul, MN (US)

( * ) Notice: Subject to any disclaimer, the term of this patent is extended or adjusted under 35 U.S.C. 154(b) by 0 days.

(21) Appl. No.: 09/335,200

(22) Filed: Jun. 17, 1999

(51) Int. Cl.$^7$ .............................................. A61B 18/04
(52) U.S. Cl. ........................... 606/34; 606/39; 606/40; 606/41; 606/42; 606/46; 606/49; 607/113; 607/115
(58) Field of Search .................... 607/96, 98, 99, 607/100, 101, 113, 115, 116, 119; 606/32, 34, 35, 39, 40, 41, 42, 46–50; 128/898

(56) References Cited

U.S. PATENT DOCUMENTS

| | | | | |
|---|---|---|---|---|
| 4,685,459 A | * | 8/1987 | Koch et al. ................... 606/51 |
| 5,341,807 A | * | 8/1994 | Nardella ..................... 128/642 |
| 5,447,529 A | | 9/1995 | Marchlinski et al. ......... 607/99 |
| 5,471,982 A | | 12/1995 | Edwards et al. ............ 128/642 |
| 5,487,385 A | | 1/1996 | Avitall ........................ 128/642 |
| 5,562,721 A | * | 10/1996 | Marchlinski et al. ......... 607/99 |
| 5,582,609 A | | 12/1996 | Swanson et al. .............. 606/39 |
| 5,598,848 A | | 2/1997 | Swanson et al. |
| 5,607,422 A | | 3/1997 | Smeets et al. ................ 606/41 |
| 5,687,723 A | | 11/1997 | Avitall ........................ 128/642 |
| 5,730,127 A | | 3/1998 | Avitall ........................ 128/642 |
| 5,836,990 A | | 11/1998 | Li |
| 5,871,523 A | | 2/1999 | Fleischman et al. .......... 607/99 |
| 6,001,093 A | * | 12/1999 | Swanson et al. .............. 606/41 |
| 6,113,595 A | | 9/2000 | Muntermann |

FOREIGN PATENT DOCUMENTS

| WO | WO 00/15130 | 3/2000 |
|---|---|---|

* cited by examiner

*Primary Examiner*—Linda C. M. Dvorak
*Assistant Examiner*—R. Kearney
(74) *Attorney, Agent, or Firm*—Fulwider Patton Lee & Utecht, LLP

(57) ABSTRACT

A method of assessing the adequacy of contact between an ablation electrode and biological tissue within a biological organ having biological fluid therein includes the steps of positioning the ablation electrode proximal the biological tissue; positioning a reference electrode a distance from the ablation electrode; measuring the impedance between the ablation electrode and the reference electrode at a first frequency and measuring the impedance between the ablation electrode and the reference electrode at a second frequency. The percentage difference between the first-frequency impedance and the second-frequency impedance provides an indication of the state of electrode/tissue contact. In general, a percentage difference of at least approximately 10% serves as an indication of substantially complete electrode/tissue contact. A percentage difference in the approximate range between 5% and 10% serves as an indication of partial electrode/tissue contact. A percentage difference less than approximately 5% serves as an indication of no electrode/tissue contact. Ratiometric measurements may also be used to assess the state of electrode/tissue contact.

51 Claims, 18 Drawing Sheets

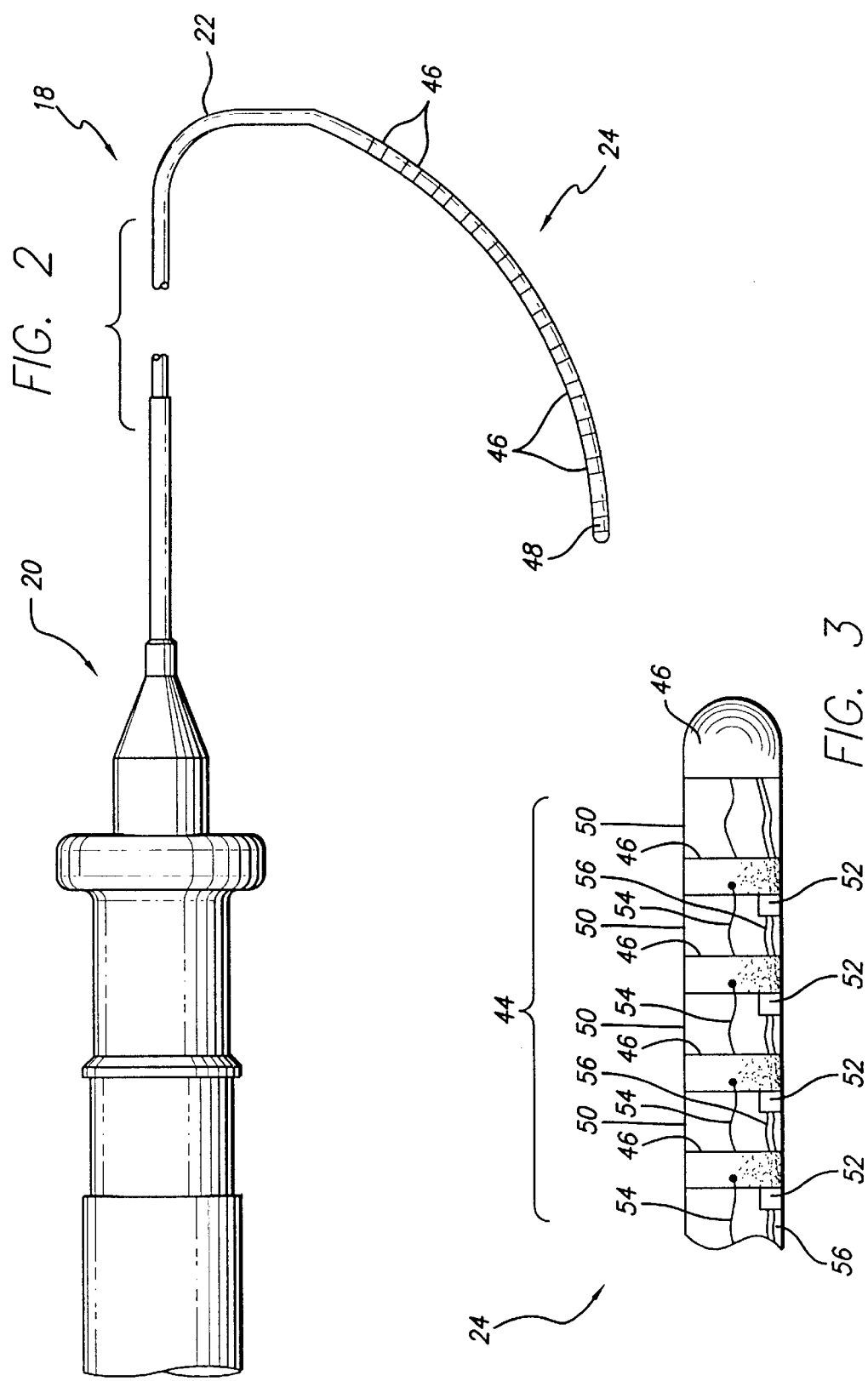

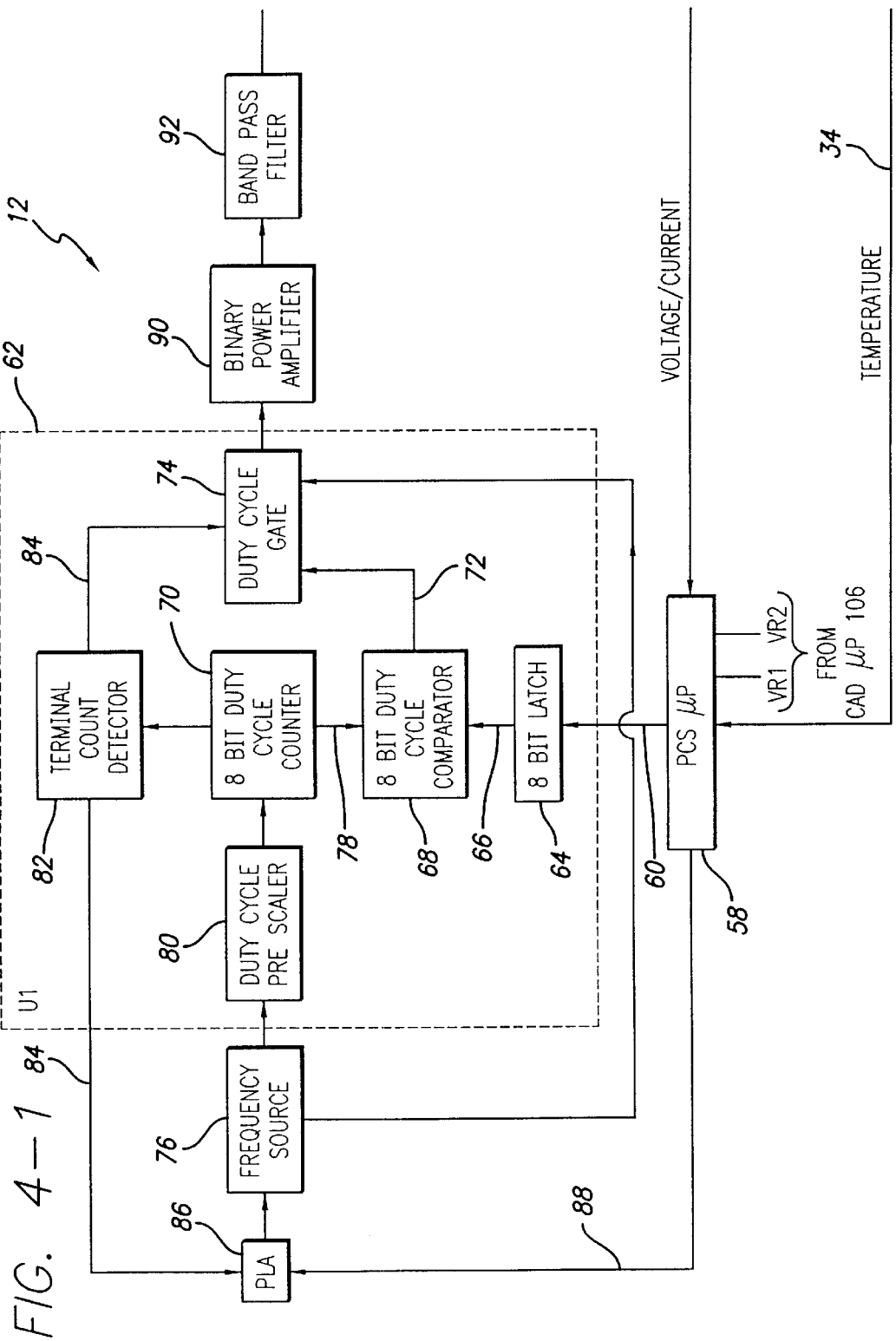

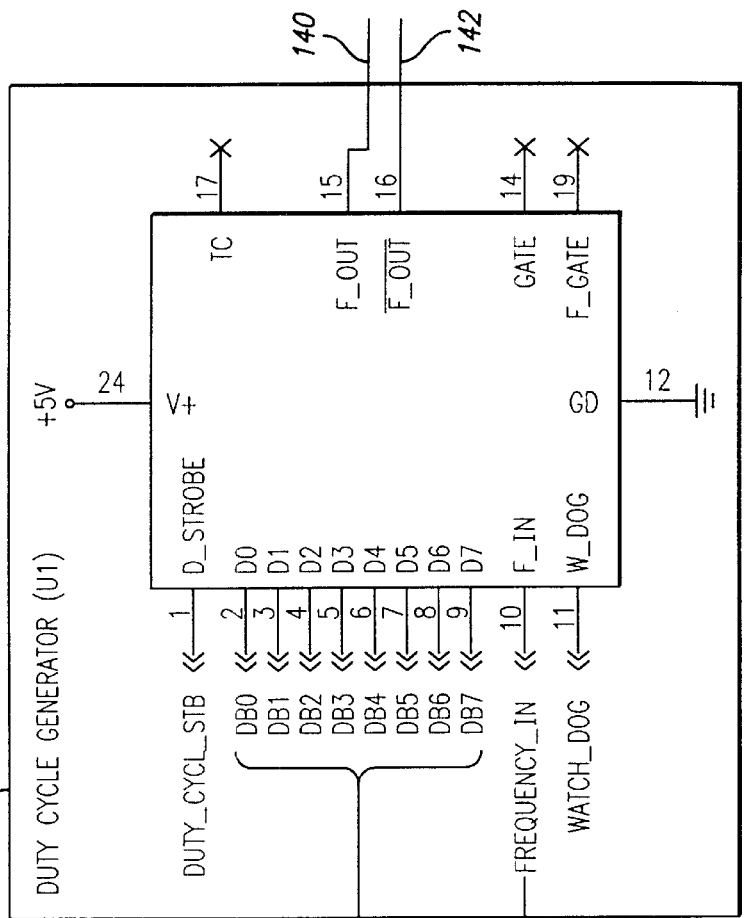
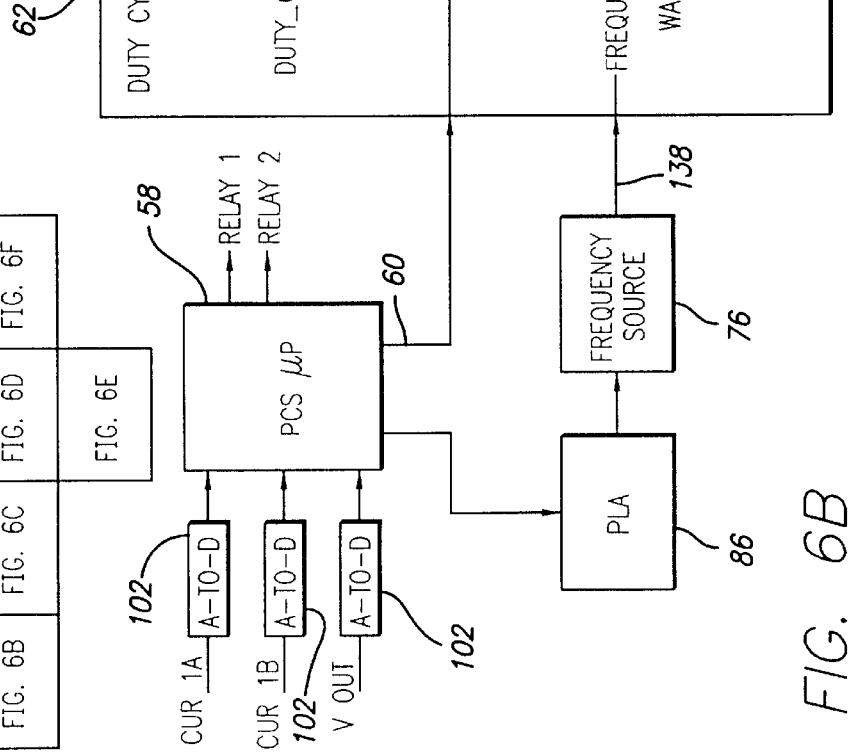
FIG. 6B

RF ABLATION APPARATUS AND METHOD HAVING ELECTRODE/TISSUE CONTACT ASSESSMENT SCHEME AND ELECTROCARDIOGRAM FILTERING

BACKGROUND OF THE INVENTION

The invention relates generally to an electrophysiological ("EP") apparatus and method for providing energy to biological tissue, and more particularly, to an EP apparatus and method for assessing the adequacy of contact between an ablation electrode and biological tissue. The invention also relates to an apparatus and method for providing energy to biological tissue while simultaneously monitoring the electrical activity within the tissue.

The heart beat in a healthy human is controlled by the sinoatrial node ("S-A node") located in the wall of the right atrium. The S-A node generates electrical signal potentials that are transmitted through pathways of conductive heart tissue in the atrium to the atrioventricular node ("A-V node") which in turn transmits the electrical signals throughout the ventricle by means of the His and Purkinje conductive tissues. Improper growth of, or damage to, the conductive tissue in the heart can interfere with the passage of regular electrical signals from the S-A and A-V nodes. Electrical signal irregularities resulting from such interference can disturb the normal rhythm of the heart and cause an abnormal rhythmic condition referred to as "cardiac arrhythmia."

While there are different treatments for cardiac arrhythmia, including the application of anti-arrhythmia drugs, in many cases ablation of the damaged tissue can restore the correct operation of the heart. Such ablation can be performed by percutaneous ablation, a procedure in which a catheter is percutaneously introduced into the patient and directed through an artery to the atrium or ventricle of the heart to perform single or multiple diagnostic, therapeutic, and/or surgical procedures. In such case, an ablation procedure is used to destroy the tissue causing the arrhythmia in an attempt to remove the electrical signal irregularities or create a conductive tissue block to restore normal heart beat or at least an improved heart beat. Successful ablation of the conductive tissue at the arrhythmia initiation site usually terminates the arrhythmia or at least moderates the heart rhythm to acceptable levels. A widely accepted treatment for arrhythmia involves the application of RF energy to the conductive tissue.

In the case of atrial fibrillation ("AF"), a procedure published by Cox et al. and known as the "Maze procedure" involves continuous atrial incisions to prevent atrial reentry and to allow sinus impulses to activate the entire myocardium. While this procedure has been found to be successful, it involves an intensely invasive approach. It is more desirable to accomplish the same result as the Maze procedure by use of a less invasive approach, such as through the use of an appropriate EP catheter system providing RF ablation therapy. In this therapy, transmural ablation lesions are formed in the atria to prevent atrial reentry and to allow sinus impulses to activate the entire myocardium.

There are two general methods of applying RF energy to cardiac tissue, unipolar and bipolar. In the unipolar method a large surface area electrode; e.g., a backplate, is placed on the chest, back or other external location of the patient to serve as a return. The backplate completes an electrical circuit with one or more electrodes that are introduced into the heart, usually via a catheter, and placed in intimate contact with the aberrant conductive tissue. In the bipolar method, electrodes introduced into the heart have different potentials and complete an electrical circuit between themselves. In the bipolar method, the flux traveling between the two electrodes of the catheter enters the tissue to cause ablation.

During ablation, the electrodes are placed in intimate contact with the target endocardial tissue. RF energy is applied to the electrodes to raise the temperature of the target tissue to a non-viable state. In general, the temperature boundary between viable and non-viable tissue is approximately 48° Centigrade. Tissue heated to a temperature above 48° C. becomes non-viable and defines the ablation volume. The objective is to elevate the tissue temperature, which is generally at 37° C., fairly uniformly to an ablation temperature above 48° C., while keeping both the temperature at the tissue surface and the temperature of the electrode below 100° C.

In order to produce effective transmural lesions it is necessary to ensure that the electrodes are in intimate contact with the tissue. Positioning of the electrodes is typically done visually under fluoroscopy imaging and is thus largely a function of a physician's training and experience. Assessment of adequate electrode/tissue contact is somewhat of an art and verification, at present, is typically inferred through comparison of pre- and post-ablation electrocardiogram ("ECG") analysis.

The use of impedance as an indication of electrode/tissue contact has been reported in the treatment of focal arrhythmias, such as ventricular tachyarrhythmia. In these procedures, a catheter with a single combination ablation/impedance-measuring tip electrode is inserted into the local blood pool within the heart and an impedance measurement is taken. The tip electrode is then placed at an ablation location and, so as to push the tip electrode deep into the cardiac tissue, force is applied along the axis of the catheter. An impedance measurement is then taken and compared to the impedance of the blood pool. This subsequent impedance measurement is referred to as a "contact-assessment" impedance. A significant increase in the contact-assessment impedance relative the blood-pool impedance serves as an indication that the tip electrode is in contact with cardiac tissue.

In this procedure a significant increase in impedance is noted due to the fact that the tip electrode is pushed deep into the cardiac tissue and is thus largely surrounded by tissue, as opposed to blood. While this electrode/tissue contact assessment technique is effective for the treatment of focal arrhythmias, it is less effective for the treatment of non-focal arrhythmias, such as atrial fibrillation. Ablation therapy for atrial fibrillation often involves the formation of transmural linear lesions. In this form of ablation therapy a linear array of band electrodes is placed against the atrial wall. While the band electrodes are held against the tissue with some degree of force, a portion of the band electrodes is likely to remain in the blood pool. The presence of blood against a portion of the band electrode affects the impedance measurement and reduces the significance of the difference between the blood-pool impedance and the contact-assessment impedance. Thus, the above-described electrode/tissue contact assessment technique that relies on the use of a tip electrode forced into the tissue is ineffective for linear ablation therapy. This known technique is further ineffective for linear ablation because it does not account for fluctuations in impedance measurements which may occur due to movement of electrodes caused by respiration and heart contractions.

As previously mentioned, in present ablation procedures, once ablation therapy is completed, the effectiveness of the therapy is verified through electrocardiogram ("ECG") analysis. Ablation therapy is completed upon the application of ablation energy for a prespecified time period. Once ablation therapy is completed, the ablation electrode is disconnected from the ablation energy source and is reconnected to an ECG amplifier/recorder. The ECG amplifier/recorder collects electrical data from the heart through the ablation electrode. The ECG amplifier/recorder analyzes the electrical data and produces signals indicative of the electrical activity through the heart tissue and particularly the ablated tissue. This present technique of assessing the effectiveness of ablation is inconvenient in that it requires ablation therapy be completed prior to assessing the ablation results and further requires physical switching from the ablation source to the ECG amplifier/recorder.

Hence, those skilled in the art have recognized a need for an RF ablation apparatus and method for assessing the adequacy of the contact between biological tissue and an ablation electrode positioned against the tissue but not necessarily completely surrounded by tissue. The need for an apparatus and a method for providing ablation energy to biological tissue while simultaneously monitoring the electrical activity within the tissue has also been recognized. The invention fulfills these needs and others.

SUMMARY OF THE INVENTION

Briefly, and in general terms, the invention is directed to an apparatus and method for assessing the adequacy of contact between an ablation electrode and biological tissue. The invention is also directed to an apparatus and method for providing energy to biological tissue while simultaneously monitoring the electrical activity within the tissue.

In a first aspect, the invention relates to a method of assessing the adequacy of contact between an ablation electrode carried by an electrode device and biological tissue within a biological organ having biological fluid therein. The method includes the steps of positioning the ablation electrode in the biological fluid; positioning a reference electrode a distance from the first electrode and the biological tissue and obtaining a reference impedance value by measuring the impedance between the ablation electrode and the reference electrode. The method further includes the steps of moving the ablation electrode to a position "proximal", i. e., near or next to, but not necessarily in contact with, the biological tissue; obtaining an assessment impedance value by measuring the impedance between the ablation electrode and the reference electrode; analyzing the assessment impedance and the reference impedance; and indicating the state of electrode/tissue contact.

In a more detailed aspect, the step of analyzing the assessment impedance and the reference impedance includes the step of calculating the percentage difference between the two impedances. Furthermore, the step of indicating the state of electrode/tissue contact includes the steps of, when the percentage difference is approximately 10% or more, indicating substantially complete electrode/tissue contact; when the percentage difference is in the approximate range between 5% and 10%, indicating partial electrode/tissue contact; and when the percentage difference is less than approximately 5%, indicating no electrode/tissue contact. In another facet, the reference impedance value is the average of a plurality of reference impedance values obtained during a given time period. In yet another facet, the assessment impedance value is the average value of a plurality of assessment impedance values obtained during a given time period. In still another detailed facet, the method further includes the step of, prior to obtaining an assessment impedance value, positioning an electrical insulator relative the ablation electrode so that when the ablation electrode is proximal the biological tissue the electrode is interposed between the electrical insulator and the tissue.

In a second facet, the invention relates to a method of assessing the adequacy of contact between a plurality of ablation electrodes carried by an electrode device and biological tissue within a biological organ having biological fluid therein. The method includes the steps of obtaining a reference impedance value by positioning the plurality of ablation electrodes in the biological fluid; positioning a first reference electrode a distance from the plurality of ablation electrodes and the biological tissue; and measuring the impedance between at least one of the ablation electrodes and the reference electrode. The method also includes the step of moving the plurality of ablation electrodes to a position proximal the biological tissue; and for each ablation electrode, obtaining an assessment impedance value by positioning a second reference electrode a distance from the ablation electrode and the biological tissue and measuring the impedance between the ablation electrode and the reference electrode; analyzing the assessment impedance and the reference impedance; and indicating the state of electrode/tissue contact.

In a third aspect, the invention relates to a method of assessing the adequacy of contact between a plurality of ablation electrodes carried by an electrode device and biological tissue within a biological organ having biological fluid therein. The method includes the steps of obtaining a reference impedance value by positioning the plurality of ablation electrodes in the biological fluid; positioning a first reference electrode a distance from the plurality of ablation electrodes and the biological tissue; and measuring the impedance between at least one of the ablation electrodes and the reference electrode. The method further includes the step of moving the plurality of ablation electrodes to a position proximal the biological tissue; obtaining an assessment impedance value by measuring the impedance between selected pairs of ablation electrodes; analyzing the assessment impedance and the reference impedance; and indicating the state of electrode/tissue contact.

In a fourth facet, the invention relates to a method of assessing the adequacy of contact between an ablation electrode and biological tissue within a moving biological organ having biological fluid therein. The method includes the steps of positioning the ablation electrode proximal the biological tissue; positioning a reference electrode a distance from the ablation electrode and applying a signal to the ablation electrode during a time period sufficient to include several movements of the organ. The method further includes the steps of obtaining a sequence of impedance values by periodically measuring the impedance between the ablation electrode and the reference electrode during the time period and monitoring the sequence of impedance values for variations indicative of electrode/tissue contact.

In a more detailed aspect, the step of monitoring the sequence of impedance values for variations indicative of electrode/tissue contact includes the steps of obtaining an average impedance value based on a plurality of the impedance values, calculating the standard deviation of the impedance values relative the average impedance and calculating a "deviation percentage." The deviation percentage is the standard deviation over the average impedance, represented as a percentage. Further included are the steps of, when the deviation percentage is at least approximately 2%, indicating substantially complete electrode/tissue contact; when the deviation percentage is in the approximate range between 1% and 2%, indicating partial electrode/tissue contact; and when the deviation percentage is less than approximately 1%, indicating no electrode/tissue contact.

In a fifth facet, the invention relates to a method of assessing the adequacy of contact between an ablation electrode and biological tissue within a biological organ having biological fluid therein. The method includes the steps of positioning the ablation electrode proximal the biological tissue; positioning a reference electrode a distance from the ablation electrode; measuring the impedance between the ablation electrode and the reference electrode at a first frequency and measuring the impedance between the ablation electrode and the reference electrode at a second frequency. The method further includes the steps of analyzing the first-frequency impedance and the second-frequency impedance and indicating the state of electrode/tissue contact.

In a more detailed facet, the step of analyzing the first-frequency impedance and the second-frequency impedance includes the step of calculating the percentage difference between the two impedances. Furthermore, the step of indicating the state of electrode/tissue contact includes the steps of, when the percentage difference is approximately 10% or more, indicating substantially complete electrode/tissue contact; when the percentage difference is in the approximate range between 5% and 10%, indicating partial electrode/tissue contact; and when the percentage difference is less than approximately 5%, indicating no electrode/tissue contact. In another facet, the step of analyzing the first-frequency impedance and the second-frequency impedance includes the steps of calculating the ratio of the two impedances and comparing the ratio to a known value. Also, the step of indicating the state of electrode/tissue contact includes the steps of, when the ratio is approximately equal to the known value, indicating no electrode/tissue contact; when the ratio deviates from the known value by an amount in the approximate range between ±0.1 to ±0.15, indicating at least partial electrode/tissue contact; and when the ratio deviates from the known value by an amount approximately greater than ±0.15, indicating substantially complete electrode/tissue contact.

In a sixth aspect, the invention relates to an apparatus for assessing the adequacy of contact between an ablation electrode carried by an electrode device and biological tissue within a biological organ having biological fluid therein. The apparatus includes a signal generating device providing as output a drive signal to the ablation electrode and a reference potential and a reference electrode spaced from the ablation electrode and responsive to the reference potential. The apparatus further includes an impedance measurement device for providing a reference impedance indicative of the impedance between the ablation electrode and the reference electrode when the ablation electrode is positioned in the biological fluid and for providing an assessment impedance indicative of the impedance between the ablation electrode and the reference electrode when the ablation electrode is positioned proximal the biological tissue; and a processor responsive to the reference and assessment impedance signals for analyzing the impedance signals and indicating the state of electrode/tissue contact.

In a seventh facet, the invention relates to an apparatus for assessing the adequacy of contact between an ablation electrode carried by an electrode device and biological tissue within a biological organ having biological fluid therein. The apparatus includes a signal generating device providing as output a drive signal to the ablation electrode and a reference signal and a reference electrode spaced from the ablation electrode and responsive to the reference signal. The apparatus further includes an impedance measurement device for providing a sequence of assessment impedance values indicative of the impedance between the ablation electrode and the reference electrode and a processor responsive to the sequence of assessment impedance signals for monitoring the sequence of impedance values for variations indicative of electrode/tissue contact.

In an eighth aspect, the invention relates to an apparatus for assessing the adequacy of contact between an ablation electrode carried by an electrode device and biological tissue within a biological organ having biological fluid therein. The apparatus includes a signal generating device providing as output a reference signal and for a first time period, a first drive signal to the ablation electrode, the first drive signal having a first amplitude and first frequency, the signal generating device also providing as output for a second time period, a second drive signal to the ablation electrode, the second drive signal having a second amplitude and a second frequency. The apparatus further includes a reference electrode spaced from the first electrode and responsive to the reference signal; an impedance measurement device for producing as output a first assessment impedance signal indicative of the impedance between the ablation electrode and reference electrode during the first time period and a second assessment impedance signal indicative of the impedance between the first and second electrodes during the second time period and a processor responsive to the first and second assessment impedance signals for comparing the impedances to a predetermined value indicative of electrode/tissue contact.

In a ninth facet, the invention relates to a method of providing ablation energy to biological tissue through an electrode device having at least one electrode while monitoring the electrical activity of the tissue. The method includes the steps of positioning the at least one electrode proximal the tissue; applying ablation power to the at least one electrode through a first lead, the ablation power comprising a high frequency component and receiving, from the electrode and through the first lead, a feedback signal indicative of the electrical activity in the tissue. The method also includes the steps of filtering the feedback signal to remove any high frequency components and providing the filtered feedback signal to an instrument through a second lead.

In a tenth aspect, the invention relates to an apparatus for providing ablation power to biological tissue through an electrode device having at least one electrode positioned proximal the tissue. The apparatus includes a generator producing ablation power having a high-frequency component; a high-frequency filter; a first lead presenting the ablation power to the at least one electrode and the filter, the first lead further presenting a feedback signal from the electrode to the filter and a second lead presenting a filter output to an instrument.

In an eleventh facet, the invention relates to an apparatus including a generator producing a plurality of ablation power signals, each having a high frequency component; a plurality of high-frequency filters; an electrode device having a plurality of electrodes; a plurality of first leads, each presenting one of the ablation power signals to one of the electrodes and one of the filters, the first lead further presenting a feedback signal from the electrode to the filter; and a plurality of second leads, each presenting a filter output to an instrument.

These and other aspects and advantages of the invention will become apparent from the following detailed description and the accompanying drawings, which illustrate by way of example the features of the invention.

BRIEF DESCRIPTION OF THE DRAWINGS

FIG. 2, is a diagram of the catheter system of FIG. 1 including a handle and a catheter sheath having a preformed distal segment carrying a linear array of electrodes;

FIG. 3 is a detailed schematic block diagram of a portion of the distal segment of FIG. 2, depicting a tip electrode and several band electrodes;

FIGS. 4-1 and 4-2 form a block diagram presenting more detail of a PCS including phase angle control, duty cycle control and impedance and temperature monitoring circuitry and a CAD including square-wave conditioning, current sense and relay control circuitry;

FIGS. 5-1 and 5-2 form a diagram of a multi-channel ablation apparatus wherein a single PCS microprocessor controls the application of ablation energy to each channel individually and a single CAD microprocessor controls the monitoring of impedances between select electrodes and/or backplates;

FIGS. 6A, 6B, 6C, 6D, 6E and 6F form a schematic diagram of an embodiment of a PCS including an ECG filter, with FIG. 6A showing how FIGS. 6B, 6C, 6D, 6E and 6F are related;

FIGS. 7-1 and 7-2 form a schematic block diagram of an embodiment of a CAD;

DETAILED DESCRIPTION OF PREFERRED EMBODIMENTS

Figure 1:
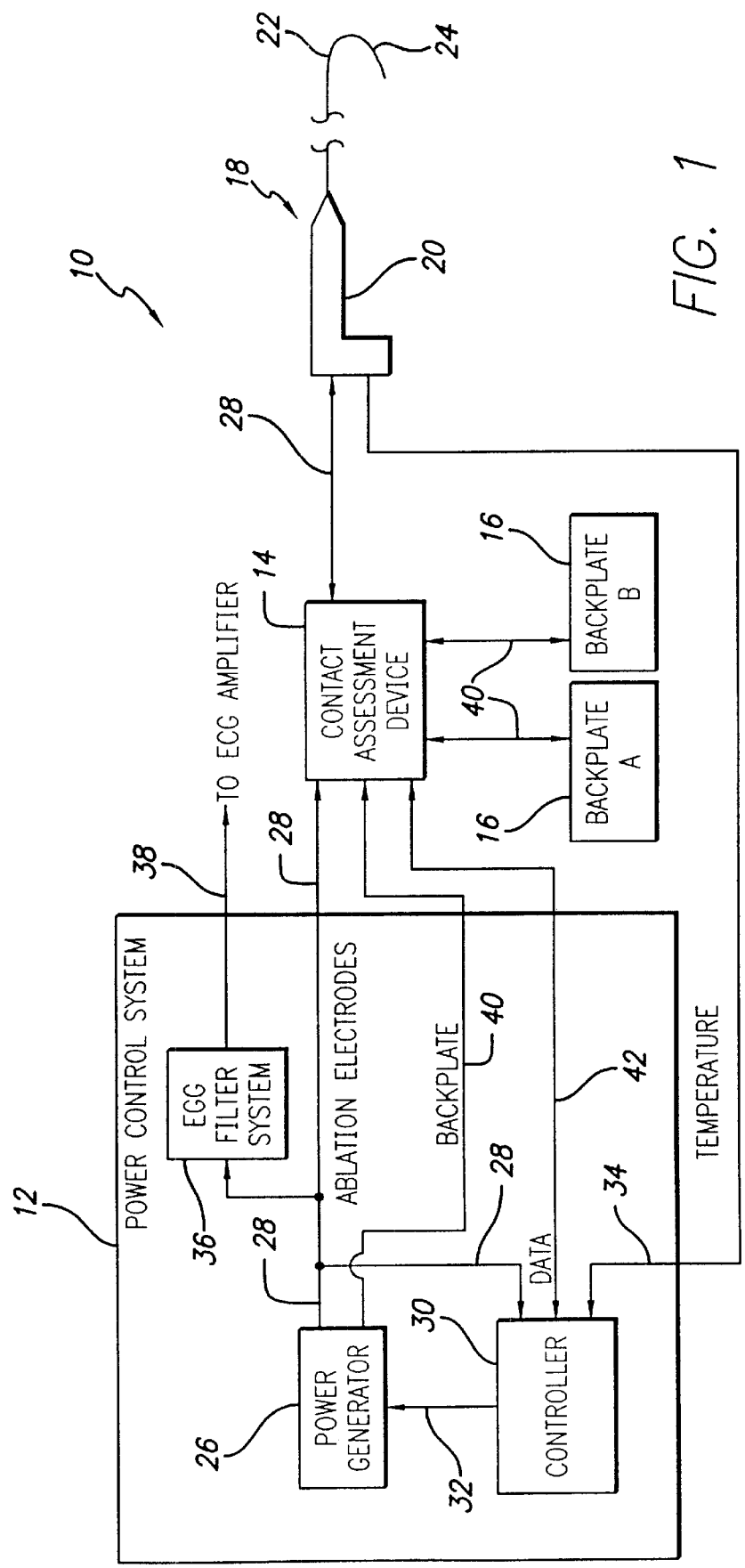
FIG. 1 is a schematic block diagram of an ablation apparatus including a power control system ("PCS") with an electrocardiogram ("ECG") filter system, a contact assessment device ("CAD"), a catheter system and backplates.

Turning now to the drawings, in which like reference numerals are used to designate like or corresponding elements among the several figures, in FIG. 1 there is shown an apparatus 10 for use in ablation therapy of a biological site, e.g., the atrium or ventricle of the heart. The apparatus 10 includes a power control system 12, a contact assessment device ("CAD") 14, a pair backplates 16 and a catheter system 18. The catheter system 18 includes a handle 20 and a steerable catheter sheath 22 having a distal segment 24. The distal segment 24 carries at least one electrode (not shown). The distal segment 24 is capable of being percutaneously introduced into a biological site.

The power control system 12 comprises a power generator 26, that may have any number of output channels through which it provides power or drive 28. The operation of the power generator 26 is controlled by a controller 30 which outputs control signals 32 to the power generator 26. The controller 30 monitors the power 28 provided by the power generator 26. In addition, the controller 30 also receives temperature signals 34 from the catheter system 18. Based on the power 28 and temperature signals 34 the controller 30 adjusts the operation of the power generator 26.

The power 28 is input to the CAD 14 and to an electrocardiogram (ECG) filter system 36 contained within the power control system 12. As explained further below, the ECG filter system 36 filters the power 28 to provide ECG signals 38 for ECG analysis. The ECG filter system 36 outputs the ECG signals 38 to the contact assessment device 14. The ECG signals 38 are then passed to an ECG amplifier (not shown). The contact assessment device 14 provides the power 28 to the catheter system 18. The CAD 14 also provides a return path 40 from the backplates 16 to the power generator 26. As explained further below, the CAD 14 collects data 42 from the catheter system 18 and provides it the controller 30. This data 42 is used to assess the adequacy of the contact between the catheter system 18 electrode or electrodes (not shown) and the biological tissue to be ablated.

Figures 2, 4:
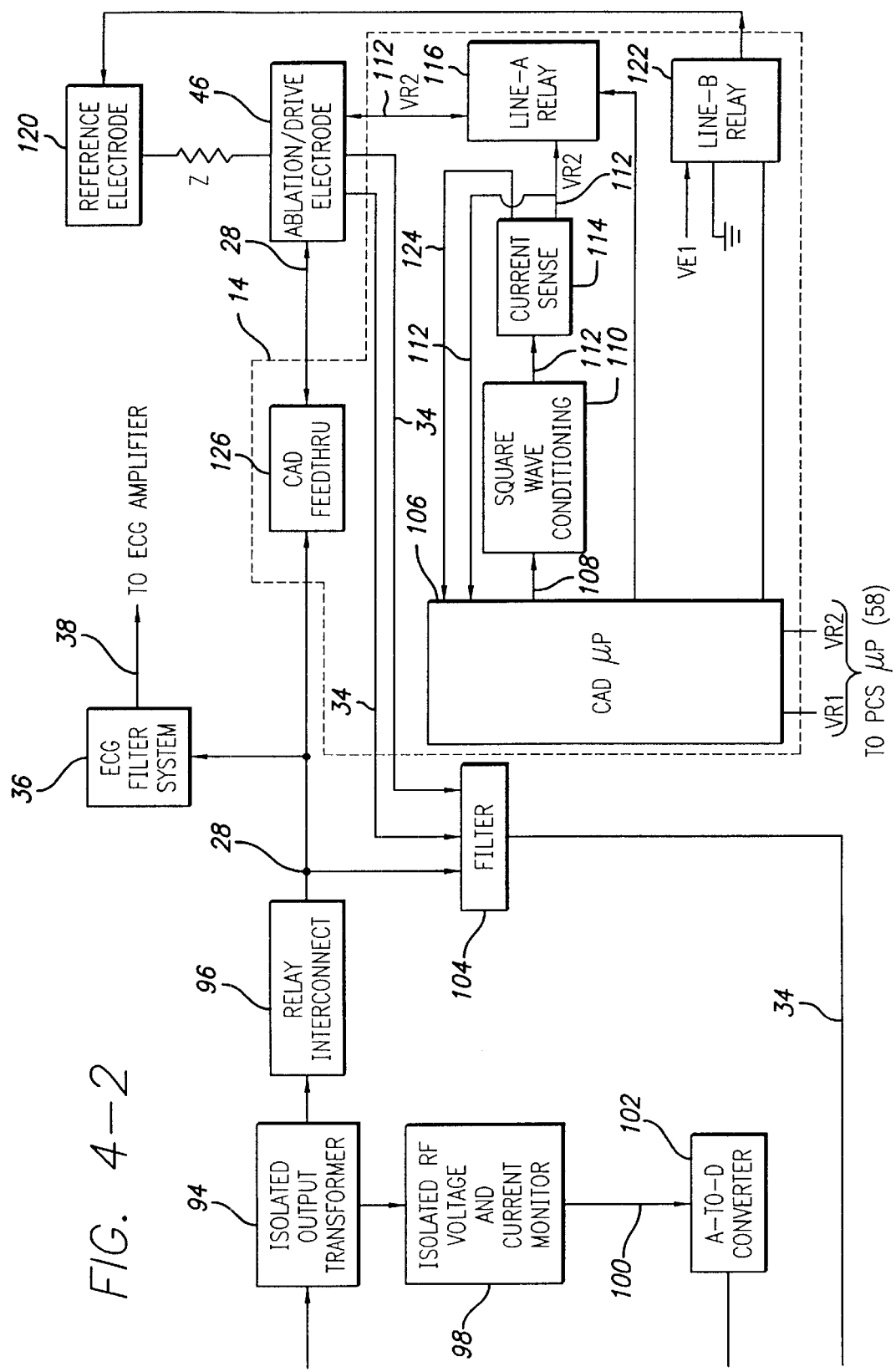

As shown in FIGS. 2. and 3, the distal segment 24 of the catheter system 18 includes an electrode device 44 (FIG. 3). The electrode device 44 is shown in schematic form with the components drawn to more clearly illustrate the relationship between the components. A preferred embodiment of the electrode device 44 includes twelve band electrodes 46 arranged in a substantially linear array along the distal segment 24 of the catheter sheath 22. The electrode device 44 may include a tip electrode 48. (For clarity of illustration, only four band electrodes 46 are shown in FIG. 3 although as stated, a preferred embodiment may include many more.) The band electrodes 46 are arranged so that there is space 50 between adjacent electrodes. In one configuration of the electrode device 44, the width of the band electrodes 46 is 3 mm and the space 50 between the electrodes is 4 mm. The total length of the electrode device 44, as such, is approximately 8 cm.

The arrangement of the band electrodes 46 is not limited to a linear array and may take the form of other patterns. A substantially linear array is preferred for certain therapeutic procedures, such as treatment of atrial fibrillation, in which linear lesions of typically 4 to 8 cm in length are desired. A linear array is more easily carried by the catheter sheath 22 and also lessens the size of the catheter.

The band electrodes 46 are formed of a material having a significantly higher thermal conductivity than that of the biological tissue to be ablated. Possible materials include silver, gold, chromium, aluminum, molybdenum, tungsten, nickel, platinum, and platinum/10% iridium. Because of the difference in thermal conductivity between the band electrodes 46 and the tissue, the electrodes cool off more rapidly in the flowing fluids at the biological site. The power supplied to the band electrodes 46 may be adjusted during ablation to allow for the cooling of the electrodes while at the same time allowing for the temperature of the tissue to build up so that ablation results. The band electrodes 46 are sized so that the surface area available for contact with fluid in the heart, e. g., blood, is sufficient to allow for efficient heat dissipation from the electrodes to the surrounding blood. In a preferred embodiment, the electrodes 46 are 7 French (2.3 mm in diameter) with a length of 3 mm.

Associated with the electrode device 44 are thermal sensors 52 for monitoring the temperature of the electrode device 44 at various points along its length. In one embodiment, each band electrode 46 has a thermal sensor 52 mounted to it. Each thermal sensor 52 provides a temperature signal 34 (FIG. 1) to the controller 30 which is indicative of the temperature of the respective band electrode 46 (FIGS. 2 and 3) at that sensor. In another embodiment of the electrode device 44 a thermal sensor 52 is mounted on every other band electrode 46. Thus for a catheter having twelve electrodes, there are thermal sensors on six electrodes. In yet another embodiment of the electrode device 44 every other electrode has two thermal sensors 52. In FIG. 3, which shows an embodiment having one thermal sensor for each electrode, there is shown a single power lead 54 for each electrode 46 to provide power to each electrode for ablation purposes and two temperature leads 56 for each thermal sensor 52 to establish the thermocouple effect.

Turning now to FIGS. 4-1 and 4-2, a block diagram of an ablation apparatus comprising a CAD 14 and a single channel power control system 12 for use with a catheter system having a single band electrode 46 is presented. As will be discussed in relation to other figures, an ablation apparatus may include a multi-channel power control system 12 for use with a catheter system having a plurality of band electrodes 46. In FIG. 4-1, a power control system ("PCS") microprocessor 58, which is part of the controller 30 (FIG. 1), provides a duty cycle control signal 60 to a duty cycle generator ("DCG") 62. In this case, the duty cycle generator 62 receives the control signal 60 by an 8-bit latch 64. The latch 64 provides an 8-bit signal 66 to a duty cycle comparator 68. The comparator 68 compares the 8-bit signal 66 to a count 78 from an 8-bit duty cycle counter 70 and if the count is the same, provides a duty cycle off signal 72 to the duty cycle gate 74. The gate 74 is connected to a frequency source ("FS") 76, such as an oscillator that produces 500 kHz. When the gate 74 receives the duty cycle off signal 72 from the comparator 68, it stops its output of the frequency source signal through the gate and no output exists.

At a frequency of 500 kHz, an 8-bit control has a period or time frame of 0.5 msec. At a fifty-percent duty cycle, the electrode is in the off period only 0.25 msec. To allow for greater cooling of the electrode, the period or time frame is lengthened by use of a prescalar 80 interposed between the frequency source 76 and the counter 70. In one embodiment, the prescalar 80 lengthens the period to 4 msec thus allowing for a 2 msec off period during a fifty-percent duty cycle. This results in a sufficient cooling time for the very thin band electrodes discussed above. Other lengths of the period may be used depending on the circumstances. It has been found that a ten percent duty cycle is particularly effective in ablating heart tissue. The combination of the application of high peak power, a ten percent duty cycle, the use of high thermal conductivity material in the band electrodes, and fluids flowing past the band electrodes which have a cooling effect on the electrodes result in a much more effective application of power to the tissue. Ablation occurs much more rapidly.

A terminal count detector 82 detects the last count of the period and sends a terminal count signal 84 to the gate 74 which resets the gate for continued output of the frequency source signal. This then begins the on period of the duty cycle and the counter 70 begins its count again. In one preferred embodiment, the duty cycle is set at fifty percent and the 8-bit latch is accordingly set to 128. In another embodiment, the duty cycle is set at ten percent.

A programmable logic array ("PLA") 86 receives phase control signals 88 from the PCS microprocessor 58 and controls the phase of the frequency source 76 accordingly. In one embodiment, the PLA 86 receives the terminal count signal 84 from the terminal count detector 82 and only permits phase changes after receiving that terminal count signal.

The output signal from the gate 74 during the on-period of the duty cycle is provided to a binary power amplifier ("BPA") 90 that increases the signal to a higher level, in this case, 24 volts. The amplified signals are then filtered with a band pass filter ("BPF") 92 to convert the somewhat square wave to a sine wave. The band pass filter 92 in one embodiment is centered at 500 kHz. The filtered signal is then provided to an isolated output transformer ("IOT") 94 that amplifies the signal to a much higher level, for example 350 volts peak-to-peak. This signal is then sent to a relay interconnect ("RI") 96 before it is provided as a power output signal OUTn 28 to the CAD 14 and the ECG filter system 36. At the CAD 14, the power output signal 28 is fed thru a CAD feedthru 126 to an electrode 46.

The power output signal 28 from the isolated output transformer 94 is monitored in one embodiment to determine the impedance at the electrode 46. In the embodiment shown in FIGS. 4-1 and 4-2, a voltage and current monitor ("VCM") 98 is used. The monitor signal 100 is converted to digital form by an A-to-D converter ("ADC") 102 and provided to the PCS microprocessor 58. As previously mentioned, some or all of the electrodes 46 may include a thermal sensor 52 (FIG. 3) that provides temperature signals 34 (FIG. 4-2) which are used to determine the temperature at the electrode 46. In one embodiment of the invention, the power 28, in conjunction with the temperature signals 34, are used to determine the temperature at the electrode 46. Both the temperature signals 34 and the power 28 pass through a temperature filter ("FL") 104 before being sent to the PCS microprocessor 58. In the alternative, the temperature filter 104 is contained in a printed circuit board separate from the controller 30 and contains its own processor. In either case, the filter 104 filters out any RF noise present in the power 28 so that the signal may be used for temperature monitoring purposes. In another embodiment, the PCS microprocessor 58 monitors the power 28 and temperature signals 34 only during the off periods of the power 28 duty cycle. Accordingly, negligible RF noise is present in the power line and filtration is not necessary. In either embodiment, the PCS microprocessor 58 may alter the duty cycle of the power 28 in response to either or both of the impedance or temperature signals.

At the ECG filter system 36 the power signal 28 is filtered to remove the 500 kHz frequency component, thus providing an ECG signal 38 that is free of high frequency interference. The ECG signal thus comprises low frequency, typically between 0 and 250 Hz, electrical signals detected in the biological tissue by the ablation electrode. As explained below, the ECG filter system 36 allows for continuous ECG analysis of the tissue to occur simultaneously with the application of ablation energy.

The CAD 14 includes a CAD microprocessor 106 that generates a multi-frequency initial square-wave drive signal 108. While the following describes the drive signal 108 as being a square-wave it is understood that the drive signal may have forms other then a square wave. The initial drive signal 108 is input to a square wave conditioning circuit 110. The conditioning circuit 110 operates to center the square-wave drive signal 108 around zero volts and to reduce the amplitude of the drive signal to a non-pacing level, i. e., a level insufficient to induce pacing of the heart.

The conditioned drive signal 112 is then input to a current sense circuit 114. The current sense circuit 114 provides voltage signals 112, 124 to the CAD microprocessor 106 which are used to calculate the current passing through the current sense circuit, i. e., the drive current. The conditioned drive signal 112 is input to line-A relay circuitry 116. The line-A relay circuitry 116 is controlled by the CAD microprocessor 106. In a single-electrode catheter system, as depicted in FIG. 4, the conditioned drive signal 112 is provided to the single electrode 46, which during contact assessment, acts as a drive electrode.

A reference electrode 120, positioned a distance from the drive electrode 46, provides a reference point for impedance measurement purposes. In a single-electrode device, the reference electrode 120 is typically the backplates 16. Alternatively, the catheter may carry, in addition to the single drive electrode 46, a dedicated reference electrode 120. This dedicated reference electrode 120 may be tied, through a line-B relay circuit 122, to a CAD ground or to a signal of known voltage VEI. The conditioned drive signal 112 is fed back to the CAD microprocessor 106 where it is digitized and sent to the PCS microprocessor 58. Based on the voltage value of the fed back drive signal, the known voltage value of the reference electrode (patient ground, instrument ground or known voltage), and the previously calculated drive current, the PCS microprocessor 58 calculates the impedance between the drive electrode 46 and the reference electrode 120.

Figures 1, 5:
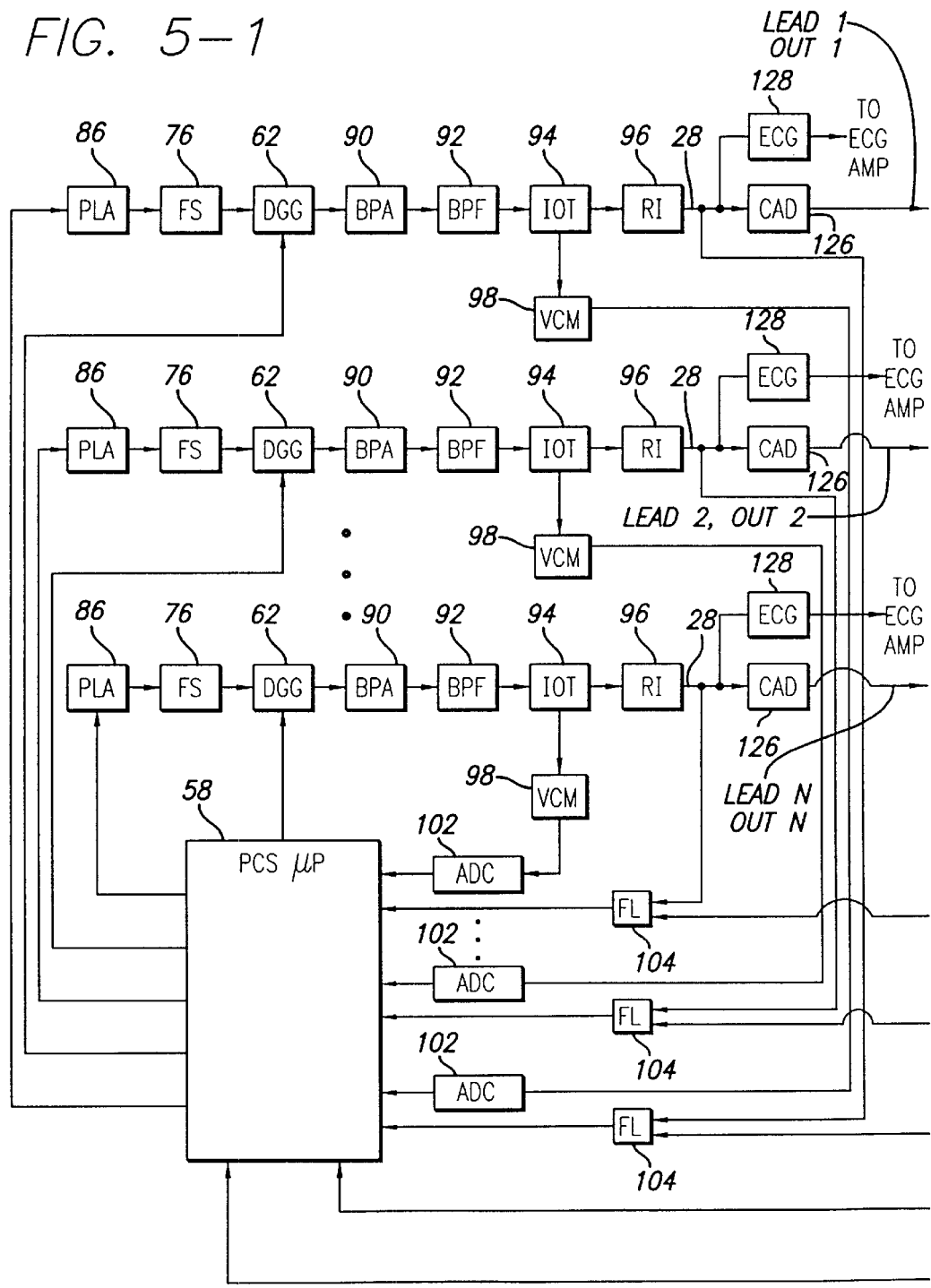
Figures 2, 5:
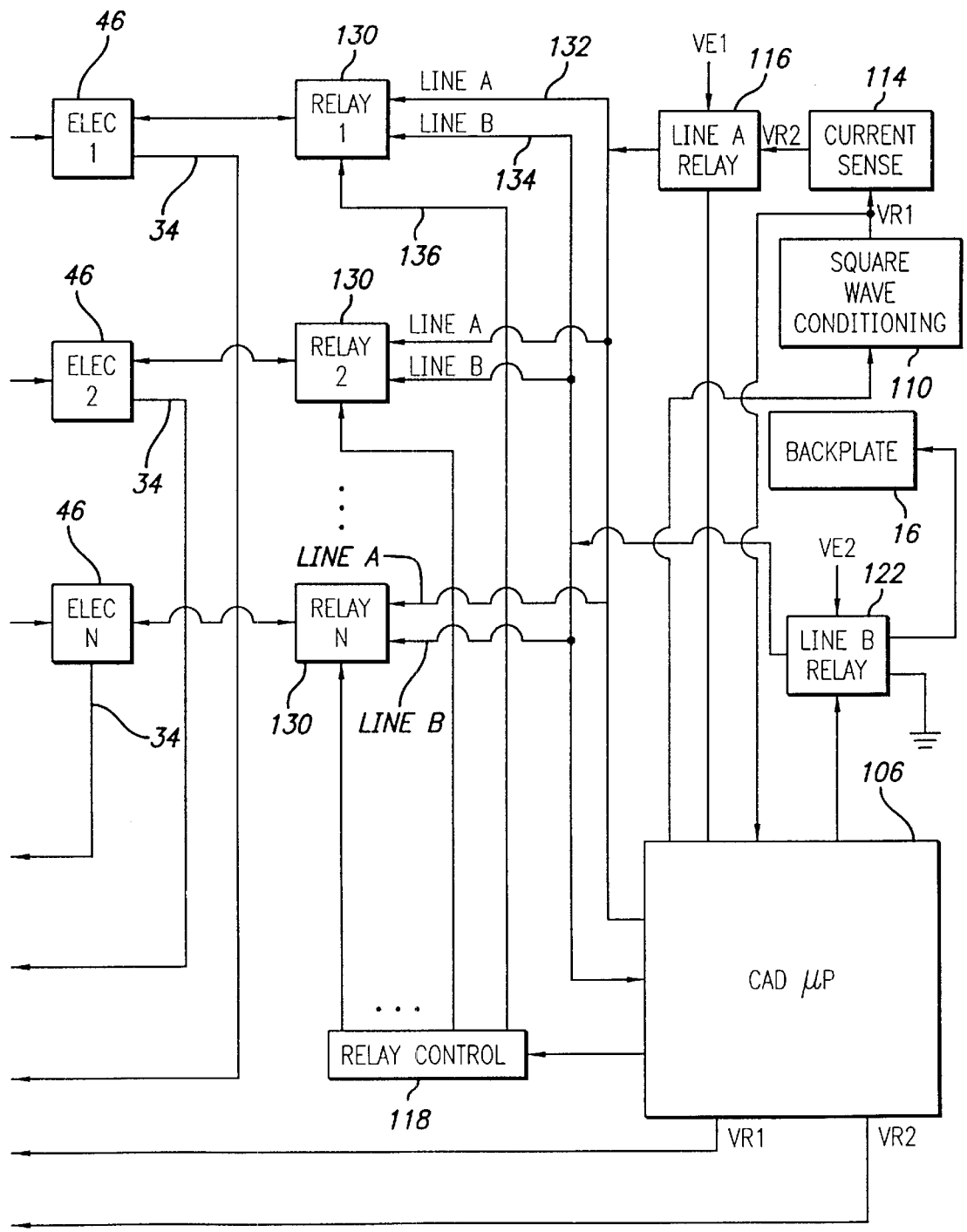

Referring now to FIGS. 5-1 and 5-2, a block diagram of an ablation apparatus having a CAD and a multi-channel power control system for use with a catheter system having a plurality of ablation electrodes 46 is shown. Although only three complete channels are shown, the apparatus comprises many more as indicated by the successive dots. Those channels are not shown in FIGS. 5-1 and 5-2 to preserve clarity of illustration.

The single PCS microprocessor 58, which again is part of the controller 30 (FIG. 1), controls the duty cycle and the phase of each channel individually in this embodiment. Each channel shown comprises the same elements and each channel produces its own power output signal 28 (OUT1, OUT2, through OUTn where "n" is the total number of channels) on respective electrode leads (LEAD 1, LEAD 2, through LEAD n where "n" is the total number of leads) to an individual ECG filter 128 and the CAD feedthru 126 to the electrode 46.

The CAD includes a plurality of electrode relays 130. Input to each of the electrode relays 130 is a line A 132, a line B 134 and relay control line 136. The line A 132 may carry either one of the conditioned drive signal 112 or an externally applied signal VE1 having a known voltage. The selection of which signal is made available on line A 132 is controlled by the line-A relay 116 under the guidance of the CAD microprocessor 106. The line A 132 provides the conditioned drive signal 112 or the external signal VE1 to a selected one of the electrodes 46 which then acts as the drive electrode, for contact assessment purposes.

Line B 134 provides a signal to one of the electrodes 46, other then the electrode which is acting as the drive electrode. Line B 134 may provide either one of the CAD ground, an externally applied signal VE2 having a known voltage, or the backplates 16. In a bipolar operation, where the impedance is measured between any pair of electrodes 46, line B 134 provides a connection path for one of the electrodes to either CAD ground or an externally applied signal of a known voltage VE2. In a unipolar operation, the line B 134 provides a connection path for one of the electrodes 46 to the backplates 16. The selection of which signal is made available on line B 134 is controlled by the line-B relay 122 under the guidance of the CAD microprocessor 106.

Operation of the electrode relays 130 is controlled by relay control circuitry 118 under the guidance of the CAD microprocessor 106. Operation of the line-A relay 116 and the line-B relay 122 is controlled directly by the CAD microprocessor 106. As explained further below, the CAD may be programmed to control the relays 116, 118, 130 to provide impedance measurements between any pair of electrodes 46 and between any one of the electrodes 46 and backplates 16. As explained below, these impedance measurements are used to assess the adequacy of electrode/tissue contact.

Figure 6C:
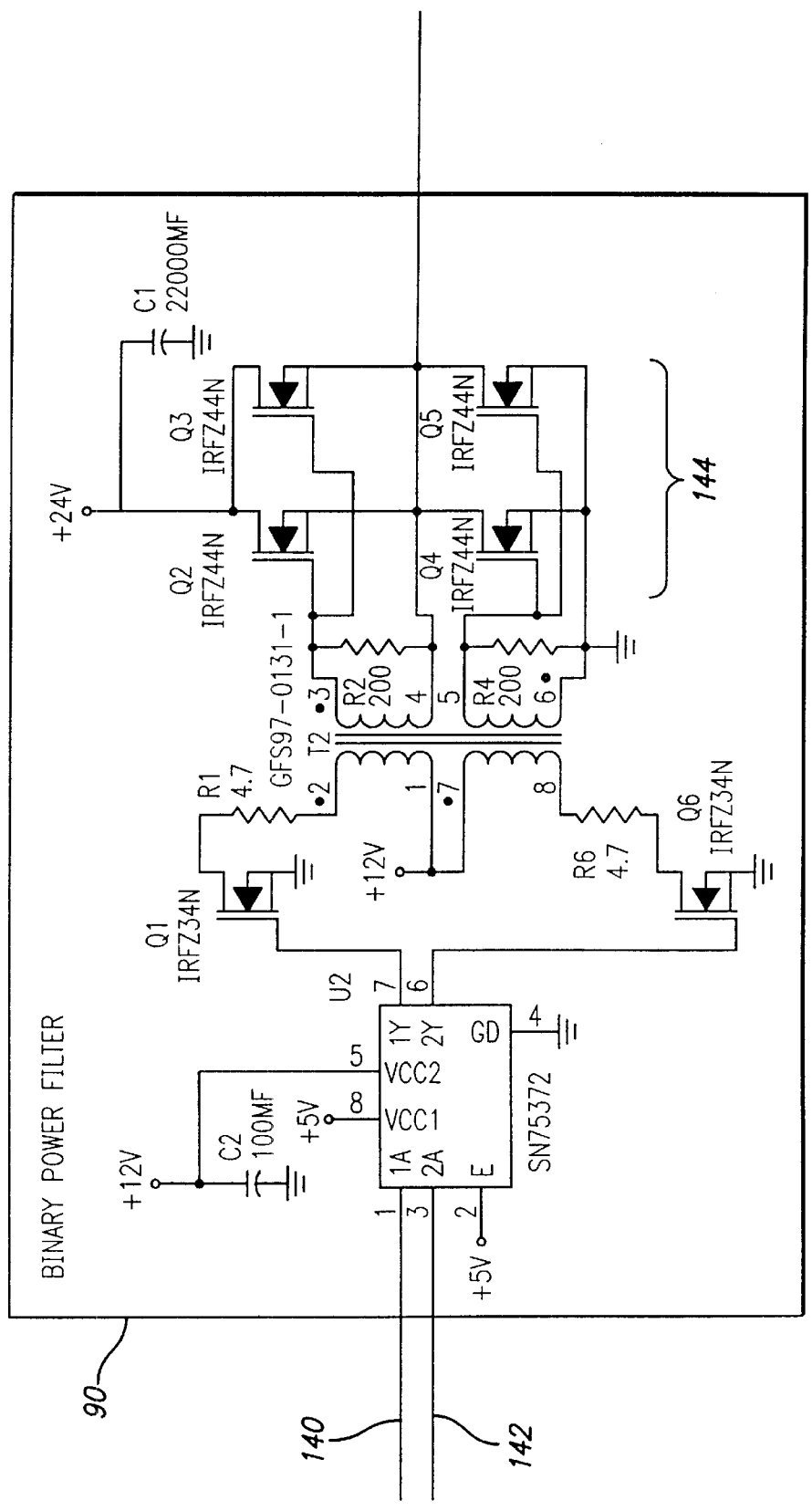
Figure 6D:
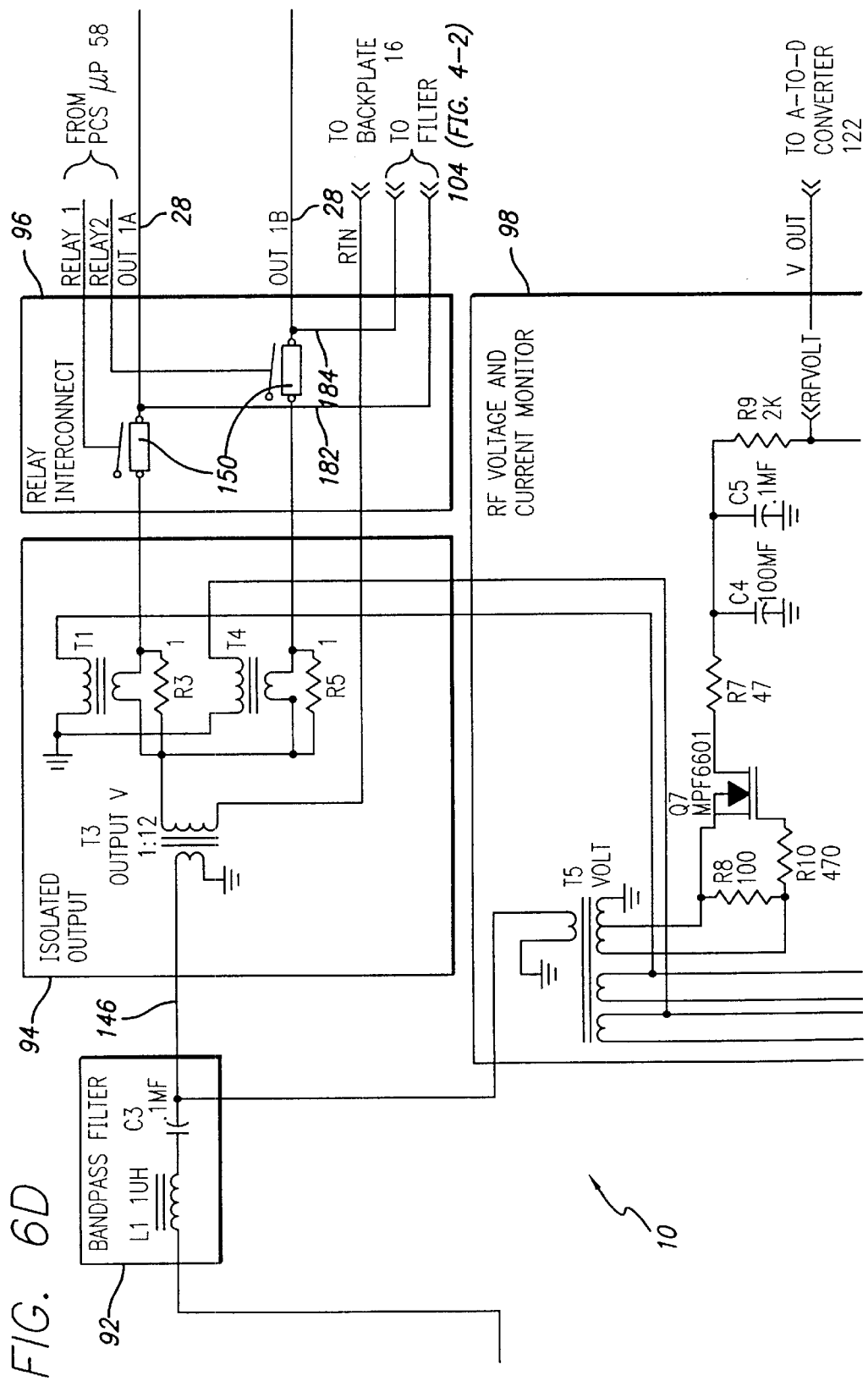
Figure 6E:
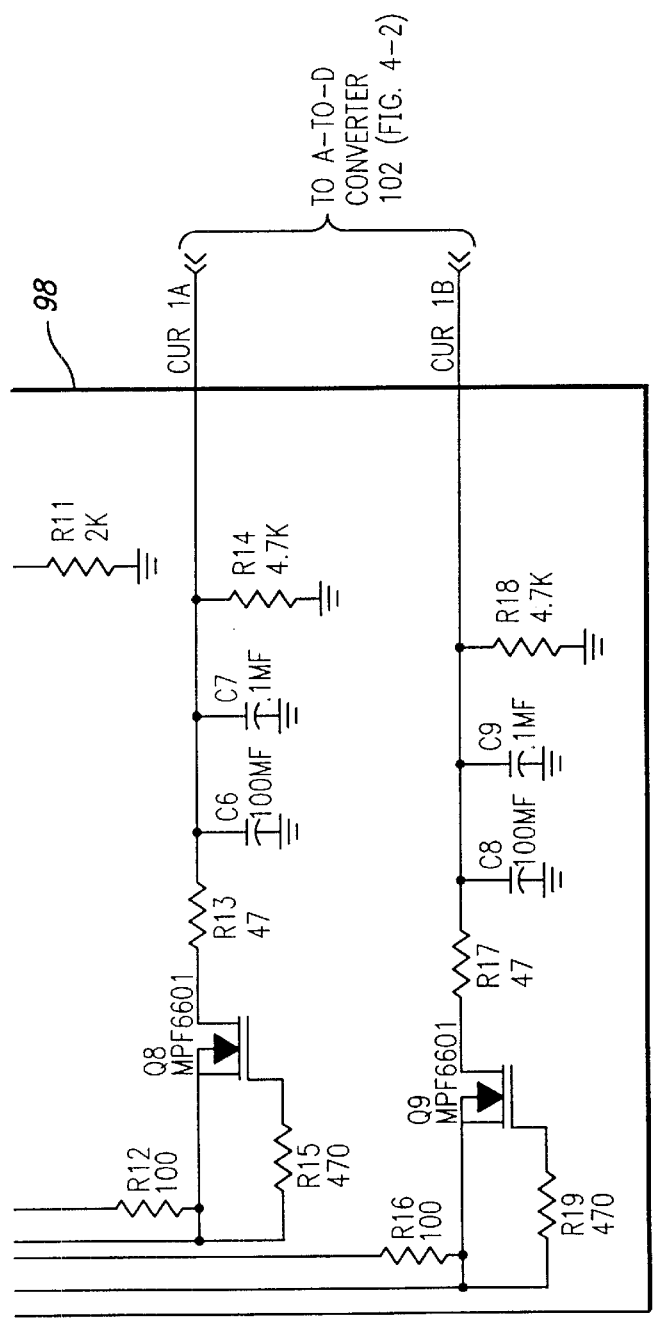
Figure 6F:
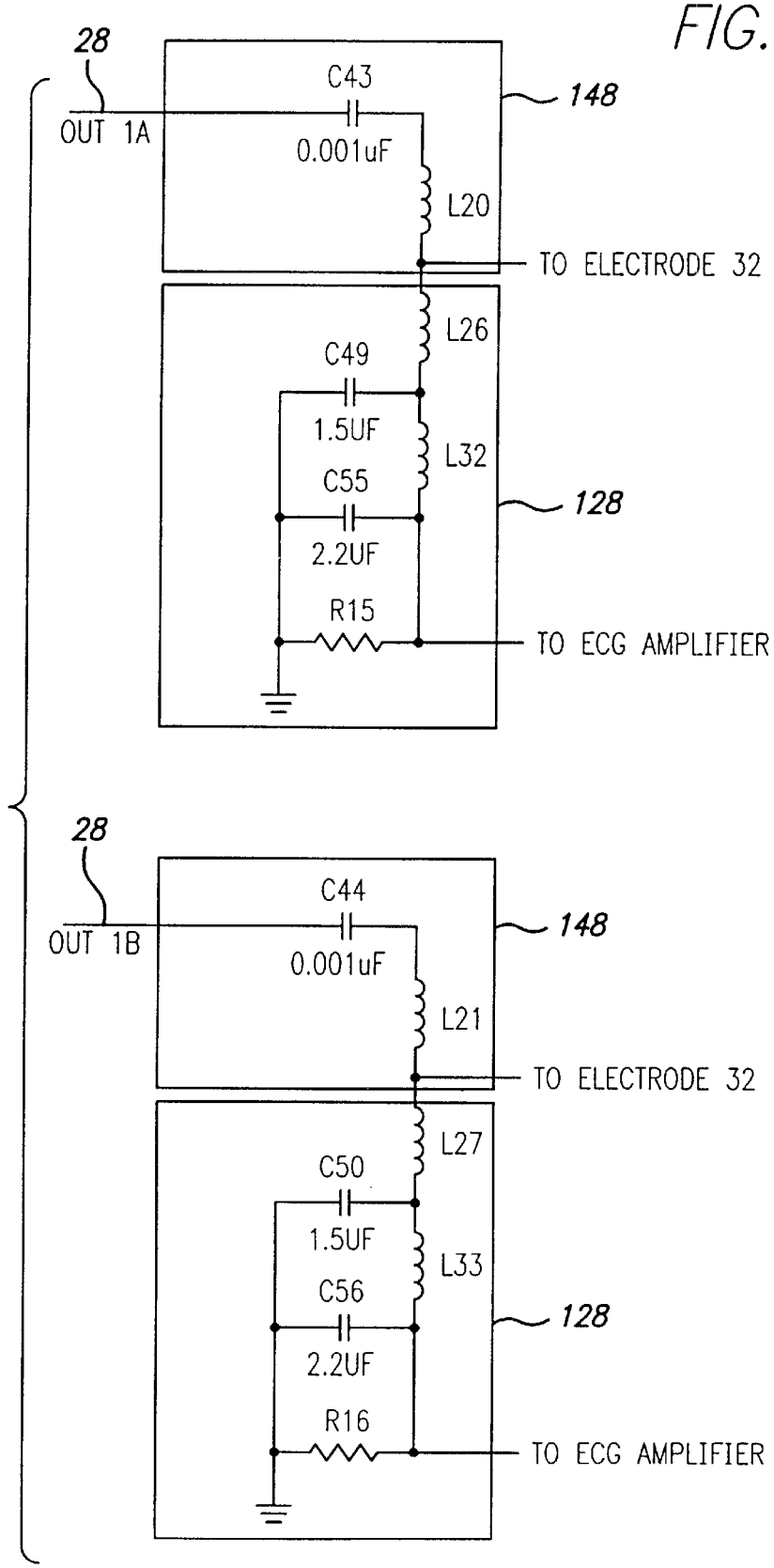

With reference now to FIGS. 6A through 6F, a schematic diagram of an embodiment of the power control system 12 of FIG. 2 is presented in FIGS. 6B through 6F while FIG. 6A shows how FIGS. 6B through 6F should be oriented in relation to each other. The frequency source 76 provides a signal 138, typically at 500 kHz with a phase angle controlled by the PCS microprocessor 58 through the PLA 86, to the duty cycle generator 62. The duty cycle generator 62 modulates the frequency source signal 138 to produce the selected duty cycle in accordance with the duty cycle control signal 60 as previously described. The duty cycle generator 62 outputs two signals 140 and 142 to the binary power amplifier 90. A dual MOSFET driver U2 receives the signals, converts their 5V level to a 12V level, and sends each to a transformer T2 which transforms the signals into 24 V peak-to-peak power.

The 24V power is then sent to a multi-state driver 144 which includes a configuration of FETs Q2, Q3, Q4, and Q5. During a conducting state of the driver 144, which is typically the on period of the power, these FETs Q2 through Q5 conduct and forward the power to a bandpass filter 92 comprising a series LC network. During a high-impedance state of the driver 144, which is typically during the off period of the power, the FETs Q2 through Q5 are nonconducting and no power is sent to the bandpass filter 92. Instead the FETs Q2 through Q5 present a high impedance load to any signals received through the electrode 46. Typically the load impedance on the FETs Q2 through Q5 presented by the circuit following the FETs, the electrode, and the tissue is approximately 150 Ω but transformed through the output transformer T3, it presents a load impedance to the FETs Q2–Q5 of approximately 0.5 to 1 Ω. In the off state, the FETs present an impedance of approximately 250 Ω which is large in comparison to the transformed load impedance of approximately 0.5 to 1 Ω. Therefore, very little power flows when the FETs are in the off state.

The bandpass filter 92 operates to shape the output signal provided by the binary amplifier 90 from a square wave to a sinusoidal wave. The filtered signal 146 then passes to the isolated output section 94 where it is step-up transformed to 350 volt peak-to-peak sinusoidal power at T3. The power is then split into two identical power signals OUT1A, OUT1B. Each of OUT1A and OUT1B is provided to an LC series resonant circuit 148 which ensures that the signal is at or near the ablation frequency, e. g., approximately 500 kHz. Each of OUT1A and OUT1B is then provided to two or more respective band electrodes 46 on the output lines LEAD1A, LEAD1B.

During ECG analysis, feedback signals from the band electrodes 46 are input to an ECG filter 128 comprising a $4^{th}$ order Butterworth filter. These feedback signals comprise generally low-frequency signals present in the biological tissue. Also input to the filter 128 is the output of the LC series resonant circuit 148, which is essentially the high-frequency ablation signal, which is typically around 500 kHz. The ECG filter 128 filters out the high-frequency ablation signal, leaving only lower frequency components. This signal is then fed to an ECG amplifier/recorder where the ECG activity of the biological tissue may be monitored.

The isolated output section 94 also includes relays 150 that may be individually opened to remove the power signals OUT1A, OUT1B from the electrode leads LEAD 1A, LEAD 1B when an alert condition is detected, such as high temperature or high impedance at the respective electrode 46. As previously mentioned these conditions are determined by the PCS microprocessor 58 which receives signals indicative of the temperature and impedance at each of the electrodes 46.

The power from the isolated output section 94 is monitored and representative signals are supplied to an RF voltage and current monitor 98 where in this case, the voltage and current of each output signal are measured to determine the impedance of the particular channel. The measured signals are sent to an A-to-D converter 102 (FIG. 2) before being sent to the PCS microprocessor 58 for impedance monitoring. If the impedance is above a threshold level indicative of blood clotting or boiling, the PCS microprocessor 58 sends a signal to the duty cycle generator 62 to reduce or discontinue the duty cycle of the power OUT1A, OUT1B and thus lower the effective power delivered to the electrodes 46.

Similarly, the temperature at the electrodes 46 is determined by monitoring the power and temperature signals and measuring the voltage difference between the signals. As previously mentioned, in one embodiment of the invention, these signals pass through a filter 104 (FIG. 2) before being sent to the PCS microprocessor 58. The voltage value is converted to a temperature and if the temperature is above a threshold level the duty cycle of the power 14 is reduced. In the case where a single lead is used to provide a signal which is used to determine the temperature as well as provide power to the electrode 46, the signal from the lead is received on temperature leads 87, 89 connected at the output side of the relays 150.

As shown in FIG. 5, the duty cycle of each electrode 46 may be individually controlled by the PCS microprocessor 58. As previously mentioned, based on the temperature at an electrode 46 and the current and voltage of the output signal provided to an electrode, the duty cycle of the output signal may be adjusted. For example, one electrode 46 may have a temperature requiring a duty cycle of ten percent, while another electrode may have a temperature which allows for a fifty percent duty cycle. In an embodiment in which every other electrode 46 has a thermal sensor 52, the electrodes are grouped in pairs with each electrode in the pair having the same duty cycle.

Referring to FIGS. 6B through and 6E, the following devices are shown:

| Device | Part No. | Manufacturer |
| --- | --- | --- |
| U1 | GAL6002B | Lattice |
| U2 | SN75372 | numerous |
| Q1 | 1RFZ34N | numerous |
| Q2, Q3, Q4, Q5 | 1RFZ44N | numerous |
| Q7, Q8, Q9 | MPF6601 | numerous |
| R3, R5 | 1Ω | numerous |
| T1, T4 | CMI-4810 | Corona Magnetics, Inc. |
| T2 | GFS97-0131-1 | GFS Manufacturing |
| T5 | CMI-4809 | Corona Magnetics, Inc. |

The transformer denoted by "T3" is a 1:12 turns ratio, single turn primary, step up transformer wound on a TDK core PC50EER23Z.

Figures 1, 7:
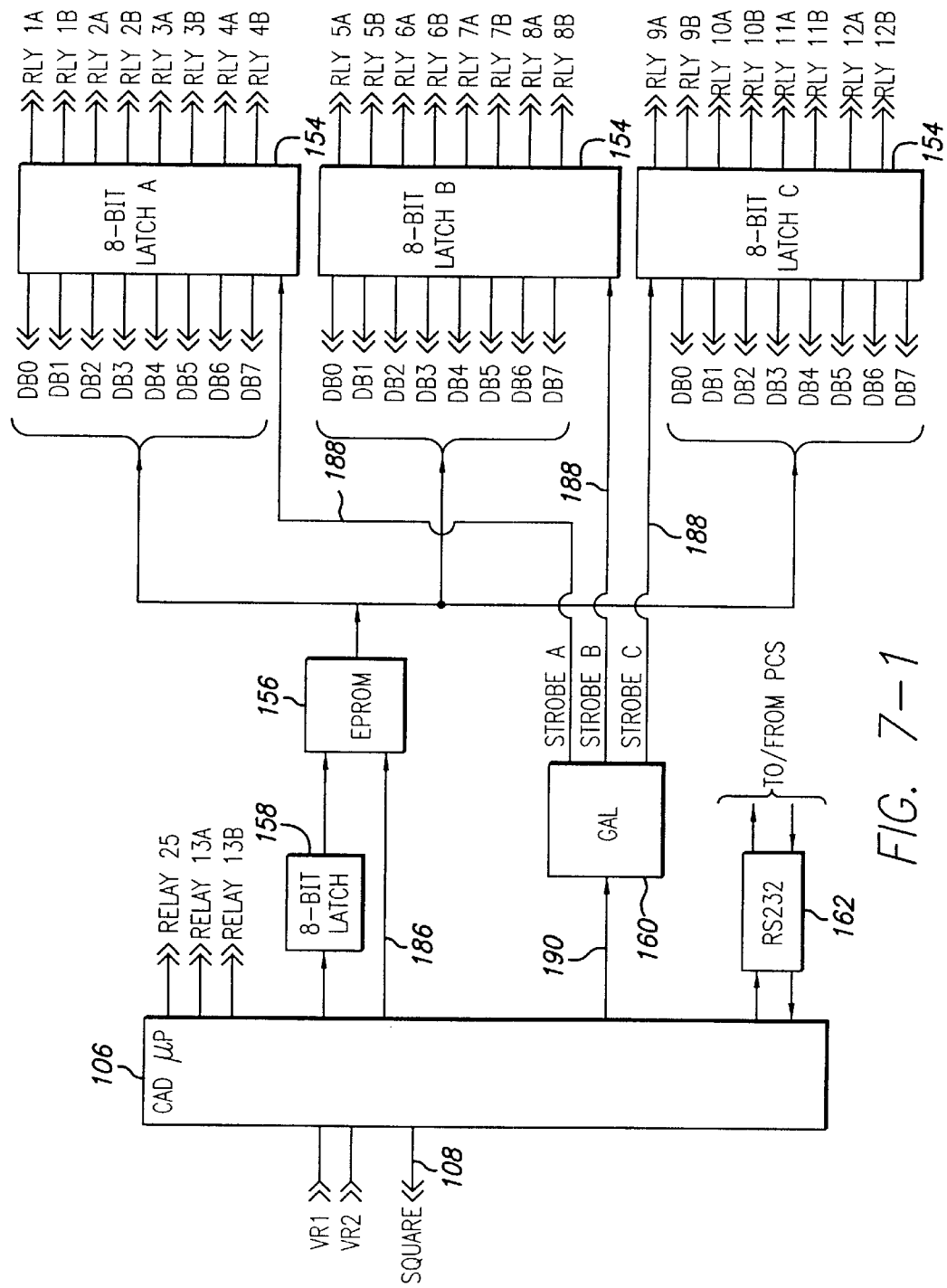
Figures 2, 7:
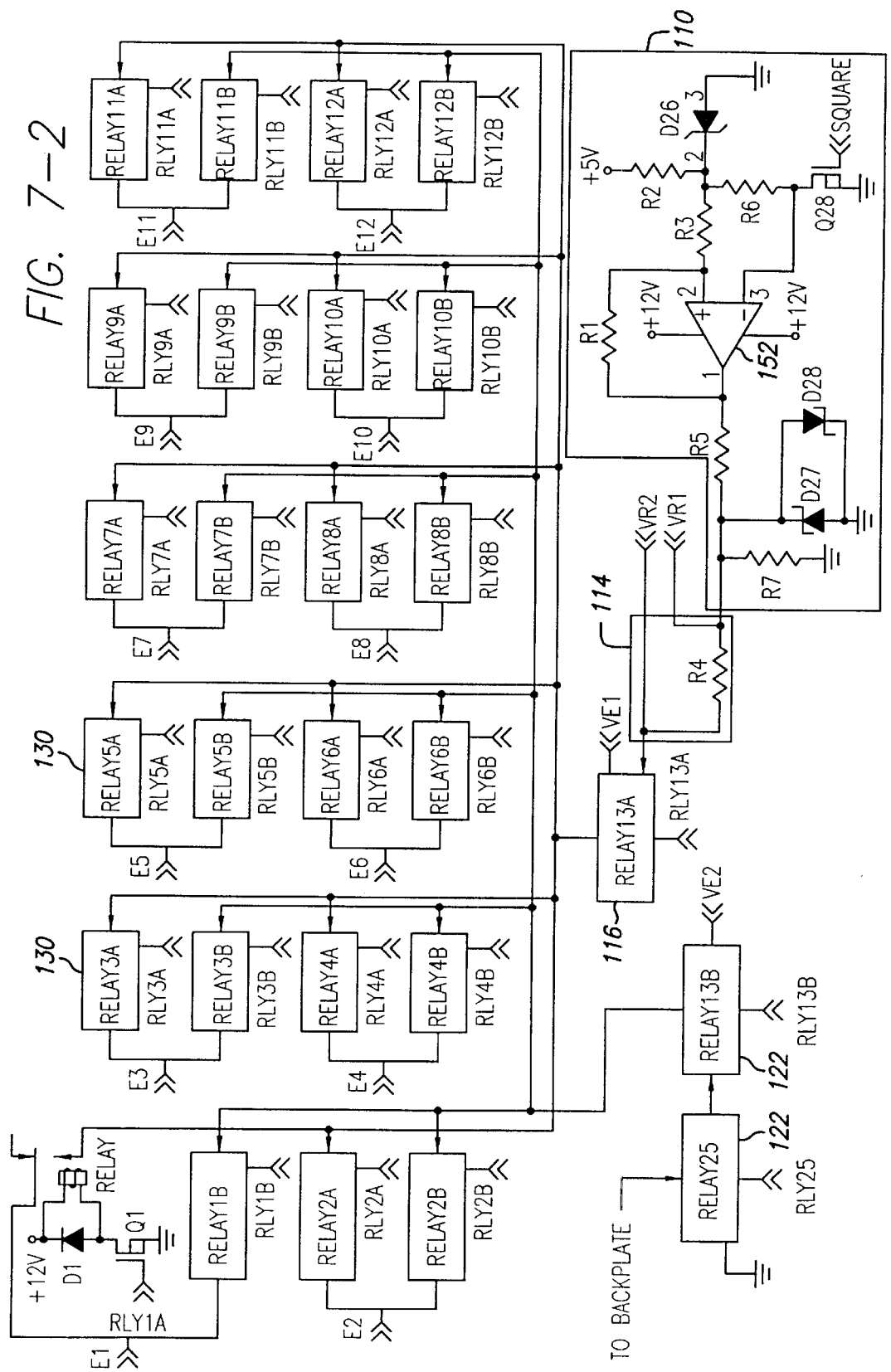

With reference now to FIGS. 7-1 and 7-2, the CAD microprocessor 106 provides a dual frequency, 5V peak-to-peak square wave at the "square" output 108. The frequencies of the signal are set by the CAD microprocessor 106 and may be changed by reprogramming the microprocessor. In a preferred embodiment, these frequencies are 10 kHz and 500 kHz. The time duration of each frequency is also set by the CAD microprocessor 106. The signal is typically set at each frequency for a portion of the total duration of the signal. For example, if the signal is output for 10 seconds, the signal is at 10 kHz for 5 seconds and at 500 kHz for the remaining 5 seconds.

The 5V square wave is input the square wave conditioning circuitry 110 that includes an offset voltage follower 152. The offset voltage follower 152 buffers and centers the 5V square wave to ±2.5 V. A voltage divider at the output of the voltage follower 152 limits the ±2.5 V square wave signal to a ±50 mV peak-to-peak square wave signal 112. This dual-frequency, 50 mV signal 112 serves as a drive signal and, prior to any impedance measurements, is available at both pins VR1 and VR2 of the CAD microprocessor 106.

The CAD 14 includes relay circuits 116, 122, 130 that allows for bipolar impedance measurements to be taken between select pairs of electrodes 46 (FIG. 5). The relay circuits 116, 122, 130 (FIG. 7-2) also allow for unipolar measurements to be taken between any of the electrodes 46 (FIG. 5) and the backplates 16. The states of the relays 116, 122, 130 are controlled by the CAD microprocessor 106. The CAD microprocessor controls relay-13A 116 and relay-13B and relay 25 122 directly. The states of the electrode relay circuits 130 are controlled through three 8-bit latch circuits 154. Data bits DB0–DB7 for controlling the electrode relays 130 are stored in the EPROM 156. The data bits DB0–DB7 are selected by the CAD microprocessor 106 through address line 186. The CAD microprocessor 106 addresses a portion of the EPROM 156 through an additional 8-bit latch 158. Upon selection, the data bits DB0–DB7 are sent to each of the 8-bit latches 154. Strobe A, B, C lines 188 from the generic array logic (GAL)160 control the activation state of the latches 154. The GAL 160, in turn, is controlled by the CAD microprocessor 106 through address line 190.

Relay 13A 116 provides for the availability of the either the drive voltage VR2 or an external voltage VE1 over line A. The external voltage VE1 is used to drive the electrodes 46 with a voltage different then the ±50 mV square wave signal. Any non-pacing voltage may be used to drive the electrode 46 to obtain impedance measurements. For example, voltages between 20 mV and 200 mV may be used in electrode/tissue contact assessment.

The closing of one of the line-A electrode relays 130 connects either VR2 or VE1 to one of the electrodes 46 which then acts as a drive electrode for impedance measurement purposes. Once this relay 130 is closed, the feedback signal from the drive electrode experiences a slight voltage drop. As explained further below, this voltage drop is used to sense the current passing between the drive electrode and another selected electrode, i. e., the reference electrode.

During the bipolar mode of impedance measurement, relay 13B and relay 122 cooperate to provide either CAD ground or an external, non-ground voltage VE2. The closing of one of the line-B electrode relays 130, connects an electrode 46 to CAD ground or VE2. This electrode 46 acts as the reference electrode. During the unipolar mode of impedance measurement, relay 13B and relay 25 122 cooperate to provide access to the backplates16 (FIG. 5) The closing of one of the line-B electrode relays 130, connects an electrode 46 to the backplates. This electrode 46 acts as the reference electrode.

The voltages VR1 and VR2 are inputs to an analog-to-digital converter in the CAD microprocessor 106. These voltages are digitized by the CAD microprocessor 106 and transmitted through the RS232 chip 162 to the PCS microprocessor 58 (FIG. 5). Initially, the PCS microprocessor 58 first determines the current passing through the current sense circuit 114 (FIG. 7) based on the difference between the voltage of the feedback signal VR2 and the drive signal VR1 and the known value of the resistor R4 contained in the current sense circuit 112. This current is essentially the same as the current passing between the drive electrode and the reference electrode.

Using this current value and the voltage difference between the drive electrode and the reference electrode, the impedance between the drive electrode and the reference electrode is calculated. The voltage difference between the drive and reference electrodes $V_{D-R}$ is usually around 50 mV when the drive electrode is maintained at VR1, i. e., substantially 50 mV, and the reference electrode is connected to either CAD ground or the backplates, i. e., patient ground. Alternatively, if the drive electrode is maintained at the externally applied voltage VE1 then $V_{D-R}$ may be a value other than 50 mV. This value depends on whether the reference electrode is connected to CAD ground, patient ground or another known voltage VE2.

Referring to FIGS. 7-1 and 7-2, the following devices are shown. Note that each of relays 1A–13B and 25 are identical. Accordingly, the parts for only relay 1A are listed.

| Device | Part No. | Manufacturer |
| --- | --- | --- |
| D26 | LM385-2-5 | Texas Instruments |
| D27, D28 | 1N5817 | Motorola |
| R1, R3 | 1.8 k Ω | numerous |
| R2 | 3 k Ω | numerous |
| R4, R7 | 10 k Ω | numerous |
| R5 | 5.6 k Ω | numerous |
| R6 | 300 Ω | numerous |
| Q28 | TN0604N3 | SuperTex |
| U11A | LF353 | Texas Instruments |
| Relay 1A: | | |
| diode Dx | 1N4004 | numerous |
| transistor Qx | TN0604N3 | numerous |
| relay | T7595D-112-12 | Potter & Bromfield |

Figure 8A:
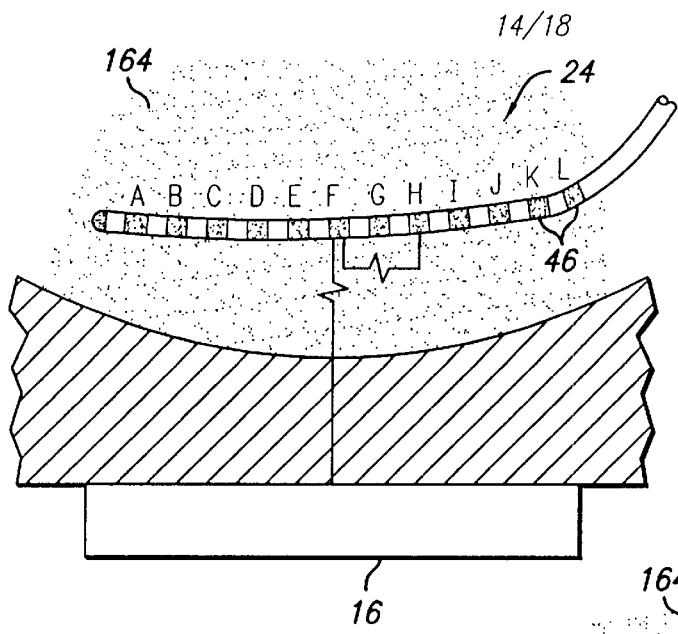
FIG. 8a is a representation of the distal segment of the catheter system of FIG. 2 positioned within a biological site and floating in the local blood pool.
Figure 8B:
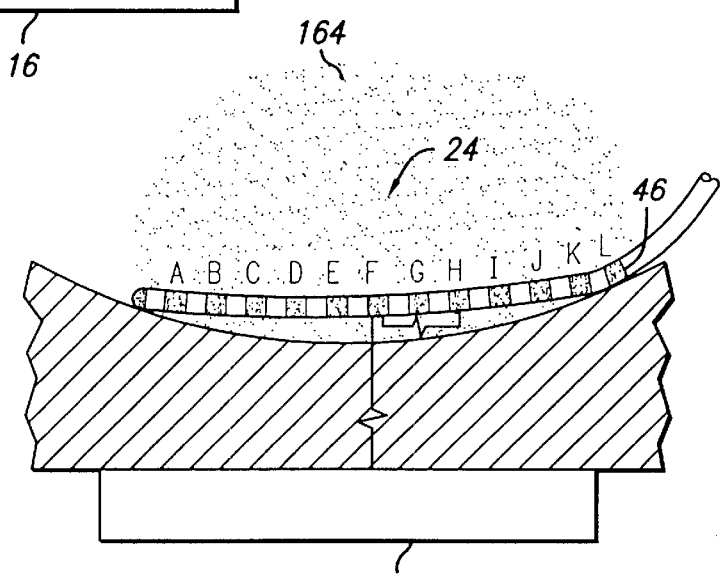
FIG. 8b is a representation of the distal segment of the catheter system of FIG. 2 positioned within a biological site and proximal biological tissue with most of the electrodes in a blood pool.
Figure 8C:
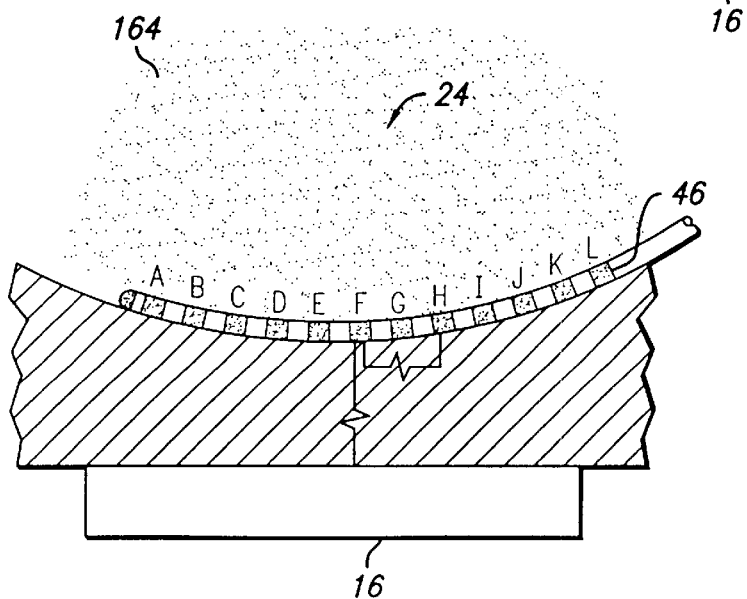
FIG. 8c is a representation of the distal segment of the catheter system of FIG. 2 positioned within a biological site and proximal biological tissue with each of the electrodes in intimate contact with the tissue.

In operation, prior to the application of RF ablation energy, the ablation apparatus of the present invention provides for electrode/tissue contact assessment. With reference to FIGS. 8a and 8c, once the distal segment 24 is positioned within the biological site, e. g., the atrium of the heart, impedance data is collected and analyzed to determine the adequacy of electrode/tissue contact.

In one embodiment of the invention, the distal segment 24 is placed near or within the atrium and positioned under fluoroscopy such that at least one of the electrodes 46 is completely within the local blood pool 164, as shown in FIG. 8a. Under CAD microprocessor 106 control, one of the electrodes 46 in the local blood pool 164 is selected to act as the drive electrode while either the backplates 16, or one of the other electrodes 46 in the blood pool is selected to act as the reference electrode. For example, as shown in FIG. 8a, electrode F may be selected as the drive electrode while either the backplate 16 or electrode H may be selected as the reference electrode. The impedance between the drive electrode and the reference electrode is then determined by applying a drive signal to the drive electrode and a reference potential to the reference electrode. As previously described this reference potential is most likely to be CAD ground or patient ground. This initial calculation provides an impedance measurement of the local blood pool 164 which serves as a reference against which subsequent impedance measurements are compared to assess electrode/tissue contact.

Experimentation has shown that impedance measurements between electrodes placed within biological fluid, e. g., blood, are generally lower than those of electrodes which contact biological tissue. With this as a guideline, once the reference impedance is determined, the distal segment 24 is repositioned, once again under fluoroscopy, such that the previously selected drive electrode, e. g. H, is positioned at a location perceived, under fluoroscopy, to be close to or in contact with tissue, as shown in FIGS. 8b and 8c. The impedance between the drive electrode and a selected reference electrode is calculated. The reference electrode is usually, although not necessarily, the same reference electrode used to calculate the reference impedance. This new impedance is referred to as an "assessment" impedance.

The assessment impedance and the reference impedance are then analyzed within the PCS microprocessor. The differences between the assessment impedance and the reference impedance is monitored for significant variations which may be indicative of tissue contact. These difference may be based on a simple mathematical difference between the impedances or may be based on a percentage change in the impedance. Experimentation has shown that an assessment impedance increase, relative the reference impedance, of between 10% and 20% is indicative of electrode/tissue contact.

In a preferred embodiment, the PCS microprocessor 58 continuously calculates both reference and assessment impedances for a given period of time and determines the average impedance for each. This period of time may be, for example, 10 seconds. Contact assessment is then based on the average impedances. In using average values, the apparatus accounts for fluctuations in impedance values that may occur due to displacement of the electrodes caused by respiration and/or heart contractions.

The PCS microprocessor analyzes the assessment impedance and the reference impedance and provides an indication of the state of the electrode/tissue contact. This indication may be provided on the front panel of the power control system through a display device. The display device may be in the form of a percentage indicative of the degree of confidence of electrode/tissue contact, with, for example, 100% indicating complete electrode/tissue contact and decreasing percentages indicating less electrode/tissue contact. Similar information may also be presented graphically by, for example, a bar graph.

The PCS microprocessor calculates the percentage difference between the two impedances and provides the following indications. When the percentage difference is at least approximately 10% the PCS microprocessor indicates that substantially complete electrode/tissue contact exists. The larger the percentage difference, the greater the level of confidence of electrode/tissue contact. When the percentage difference is in the approximate range between 5% and 10% the PCS microprocessor indicates that partial electrode/tissue contact exists. When the percentage difference is less than approximately 5% the PCS microprocessor indicates that there is no electrode/tissue contact.

The ablation apparatus 10 is particularly well suited for use with a catheter system having a linear array of band electrodes 46 at its distal segment 24. With continued reference to FIGS. 8a and 8c, once the reference impedance of the local blood pool 164 is determined, an electrode/tissue contact assessment of each electrode 46 in the linear array may occur. Beginning, for example, with electrode A and continuing in sequence though electrode L, the impedance between each electrode 46 and a selected reference electrode is measured. Each impedance is compared to the reference impedance to assess electrode/tissue contact adequacy.

As previously mentioned, the impedances are preferably measured continuously for a few seconds in order to obtain a meaningful impedance average. This average measurement effectively filtrates the impedance fluctuations induced by heart contraction and respiration. In another embodiment of the invention described next, these impedance fluctuations assist in electrode/tissue contact assessment.

Respiration and contractions of the heart tend to cause an electrode, which may be in contact with the heart tissue, to move away from the tissue. With this in mind, once the distal segment 24 is positioned proximal biological tissue, a sequence of impedance measurements are taken over a time period sufficient to include several contradictions of the heart. Experimentation has shown that by monitoring these sequences for significant variations, an assessment of electrode/tissue contact may be made. The variation of impedances due to respiration/heart contraction is most noticeable when there is electrode tissue contact. Thus a large standard deviation from the average impedance may serve as an indicator of tissue contact. On the other hand, in analyzing the sample-to-sample variations in impedance caused by heart contractions it is noted that the value corresponding to blood pool placement has a smaller range of variations and thus a small standard of deviation from the average impedance. A theory for this is that the catheter moves less simply because it is "floating" or not contacting tissue, and is less effected by respiration and by heart contraction.

The PCS microprocessor analyzes the sequence of assessment impedances and provides an indication of the state of the electrode/tissue contact. The PCS first obtains an average impedance value based on a plurality of the impedance values. The PCS then calculates the standard deviation of the impedance values relative the average impedance. Next, the PCS calculates a deviation percentage by dividing the standard deviation by the average impedance and representing the result as a percentage value. The PCS then provides the following indications. When the deviation percentage is at least approximately 2% the PCS microprocessor indicates that substantially complete electrode/tissue contact exists. The larger the deviation percentage, the greater the level of confidence of electrode/tissue contact. When the deviation percentage is in the approximate range between 1% and 2% the PCS microprocessor indicates partial electrode/tissue contact exists. When the deviation percentage is less than approximately 1% the PCS microprocessor indicates no electrode/tissue contact.

In one application of the apparatus in the right atrium, during tissue contact the average impedance during a 30 second time period was 262 Ω while the standard deviation for the sequence of impedances was 6.64. The deviation percentage was 2.5%. Without tissue contact, an average impedance of 222 Ω with a standard deviation of 1.78 was observed for the sequence of impedance values. The deviation percentage in this case was 0.8%. It is noted that when assessing contact based on a sequence of impedances it is not necessary to obtain a reference impedance, i. e., the impedance of the blood pool. Instead, the distal segment 24, may immediately be placed near the tissue and electrode/tissue contact assessment may be made.

Experimentation has shown that the frequency of the drive signal affects the impedance measurements. In general, the lower the frequency the greater the "selectivity", i. e., difference between blood-pool impedance and tissue impedance. As the frequency of the drive signal increases, the selectivity decreases. While it is desirable to have a high selectivity for contact assessment analysis, the drive-signal frequency should be kept sufficiently high enough to avoid pacing the heart. It has been observed that both voltage and frequency of the drive signal play a part in inducing pacing. In general, as the voltage level increases, the minimum frequency below which pacing is induced increases. Thus for example, for a voltage level of 50 millivolts, 10 kHz is a likely minimum, non-pacing, frequency. A frequency less than 10 kHz is likely to induce pacing. If the voltage level is increased to 100 millivolts, the minimum, non-pacing, frequency becomes greater than 10 kHz.

In another embodiment of the invention, impedance measurements are taken at two different frequencies and the variations between the two are used to assess electrode/tissue contact. This embodiment is referred to as the "dual-frequency" embodiment. The two frequencies include a low frequency and a high frequency. The low frequency is generally a frequency just above the pacing threshold of the heart and provides high selectivity. The high frequency is a frequency that is generally at least two fold greater than the low frequency and thus provides a lower selectivity. The high frequency is typically at least 100 kHz.

Experimentation has shown that variations in the frequency of the drive signal produce corresponding variations in impedance. During electrode/tissue contact, the difference between a high-frequency impedance and a low-frequency impedance is greater than the difference between the impedances at the same two frequencies when the electrode is in the blood pool. These observations are used in the dual-frequency embodiment of the invention to assess tissue contact based on the percentage differences between the low-frequency and high-frequency impedances and alternatively, based on the ratio of the high-frequency impedance to the low frequency impedance or vice versa. These two approaches are referred to respectively as the "percentage-difference" approach and the "ratiometric" approach.

In the percentage-difference approach, the distal segment 24 is positioned under fluoroscopy so as to place one or more electrodes 46 at or near the biological tissue. Similar to the other embodiments of the invention, one of the electrodes 46 acts as the drive electrode while another electrode or the backplates act as a reference electrode. The impedance between the drive electrode and the reference electrode is measured after applying a first drive signal having a first frequency to the drive electrode for a given time period. Subsequently, a second drive signal having a second frequency different from the first frequency is applied to the drive electrode for a given time period and an impedance measurement is taken. In a preferred embodiment, the first frequency is 10 kHz and the second frequency is 500 kHz and the time period for each frequency is 5 seconds.

The PCS microprocessor analyzes the first-frequency impedance and the second-frequency impedances by calculating the percentage difference between the two impedances. When the percentage difference is at least approximately 10%, the PCS microprocessor indicates that substantially complete electrode/tissue contact exists. Once again, the larger the percentage difference, the greater the level of confidence of electrode/tissue contact. When the percentage difference is in the approximate range between 5% and 10%, the PCS microprocessor indicates that partial electrode/tissue contact. When the percentage difference is less than approximately 5%, the PCS microprocessor indicates that there is no electrode/tissue contact.

In the ratiometric approach, the PCS microprocessor analyzes the first-frequency impedance and the second-frequency impedance by calculating the ratio of the two impedances. The assessment ratio is then compared to an expected, i. e., "calibration", value indicative of no electrode/tissue contact. The calibration value of a CAD is usually determined through prior use of the CAD. For example, the first time a CAD is used the impedance of blood at both the first frequency and the second frequency may be measured and the ratio of the two may serve as the calibration value. The calibration value of a CAD is typically stored in the CAD EPROM. When the assessment ratio is approximately equal to the calibration value, the PCS microprocessor indicates no electrode/tissue contact. When the ratio deviates from the calibration value by between approximately ±0.1 to ±0.15, the microprocessor indicates at least partial electrode/tissue contact. It is noted that because the analysis is based on a comparison of ratios, the manner in which the subsequent measurements deviate, i. e., greater than or less than the base line, is irrelevant to contact assessment analysis. As the assessment ratio deviates from the calibration value by a value greater than approximately ±0.15 the degree of confidence of electrode/tissue contact increases. For example, the confidence level of electrode/tissue contact for an assessment ratio of 0.25 less than the calibration value is greater than the confidence level for an assessment ratio of only 0.16 less than the calibration value. In general, when the assessment ratio deviation is greater than approximately ±0.15, the microprocessor indicates substantially complete electrode/tissue contact.

In an alternate ratiometric approach, a blood-pool ratiometric measurement is first determined by placing the electrodes in the blood pool and then calculating the ratio of the first-frequency and second-frequency impedances. The blood-pool ratiometric measurement serves as a base line against which subsequent ratiometric measurements may be compared. If subsequent ratiometric measurements are substantially equal to the base line value than the PCS microprocessor indicates no electrode/tissue contact. When the ratio deviates from the base-line value by between approximately ±0.1 to ±0.15, the microprocessor indicates at least partial electrode/tissue contact. When the assessment ratio deviation is greater than approximately ±0.15, the microprocessor indicates substantially complete electrode/tissue contact.

In each of the embodiments of the invention thus far described, the selection of drive and reference electrodes is controlled by the CAD microprocessor 106. The CAD microprocessor 106 may be programmed to select adjacent electrode pairs, e. g., A-B, B-C, C-D, etc., or far-distance electrode pairs, e. g., A-F, B-L, C-E, etc. as the drive/reference electrode pairs. Experimentation has shown that impedance between adjacent electrode pairs exhibit greater variation between tissue contact and blood pool contact states than do far-distance electrode pairs and thus provide more accurate contact assessment results.

Figure 9A:
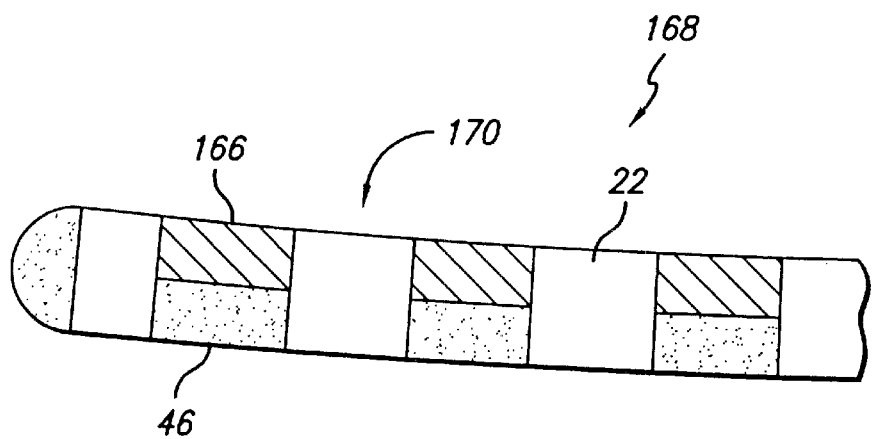
FIG. 9a is a diagram of a portion of the distal segment of a catheter system having full-ring band electrodes partially coated with an electrically insulating but thermally conductive material.
Figure 9B:
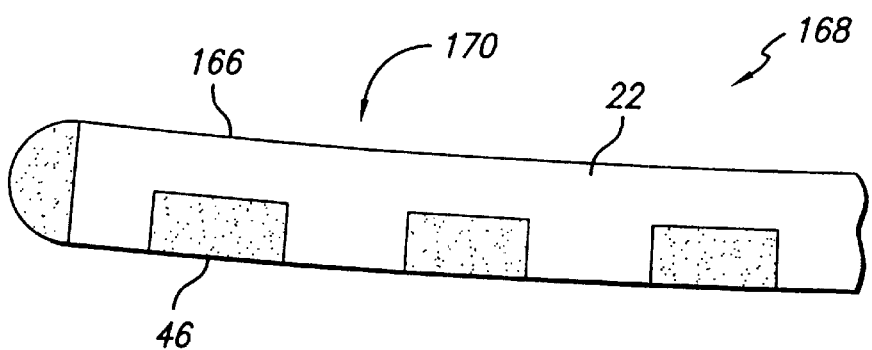
FIG. 9b is a diagram of a portion of the distal segment of a catheter system having half-ring band electrodes positioned on the outside radius of curvature.
Figure 9C:
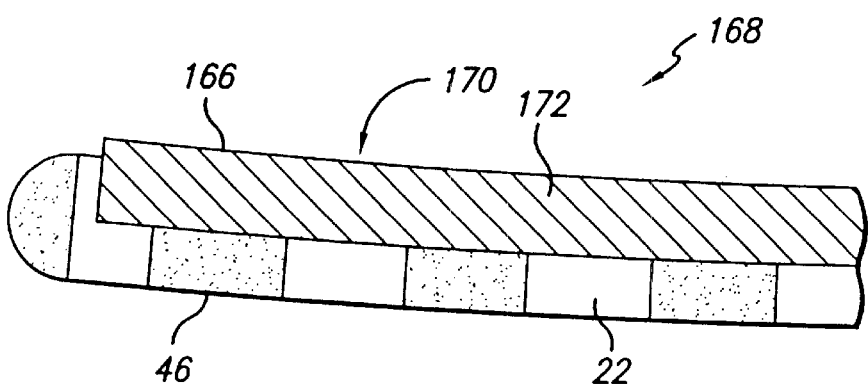
FIG. 9c is a diagram of a portion of the distal segment of a catheter system having an outer sheath comprising an insulating material partially surrounding the band electrodes.
Figure 10A:
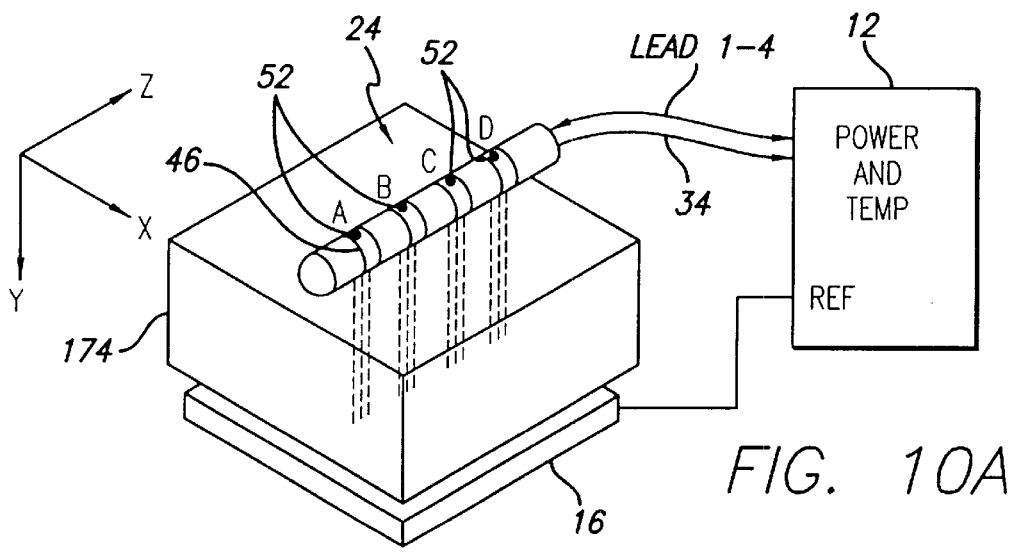
FIG. 10A is a three dimensional representation of an ablation apparatus having a linear array of band electrodes in contact with a biological site with a backplate at the opposite side of the biological site, in which the phase angle difference between adjacent electrodes of the linear array is zero degrees.
Figure 10B:
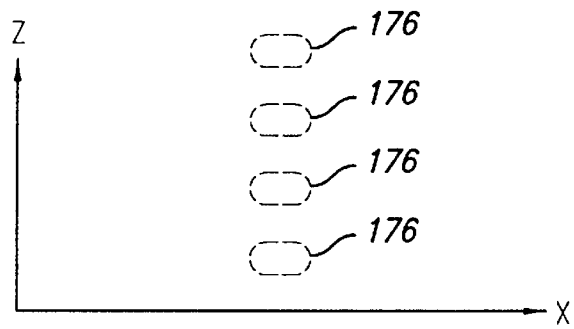
FIGS. 10B through 10D depict, along the x, y, and z axes shown, the depth of the lesions formed by the ablation apparatus of FIG. 10A showing that the apparatus acts as a unipolar device with multiple electrodes and the resulting lesions are discontinuous.
Figure 10C:
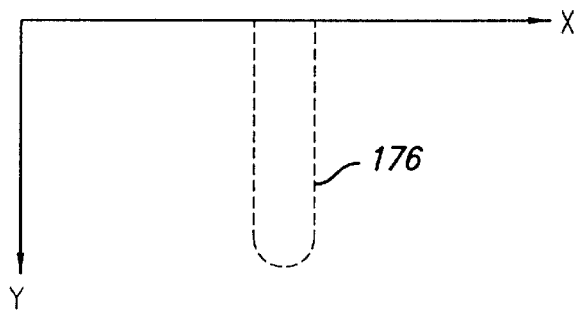
Figure 10D:
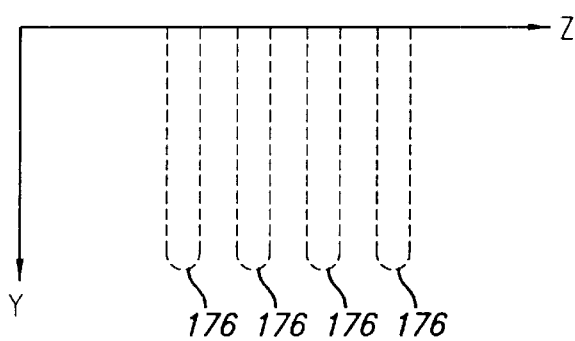

With reference to FIGS. 9a–9c, in order to increase the impedance between electrode pairs while they are in contact with tissue, the blood-side portion of the electrodes 46 may be covered with or shielded by an electrically insulating but thermally conductive material 166, such as parylene, polyimide, PTFE or other thin dielectric. The portion of the electrodes 46 selected for covering or shielding are typically on the inward side of curvature 170 of the catheter sheath 22 such that the uncovered portion of the electrode is placed in contact with the tissue. The partial coating of the electrodes 46 electrically insulates the blood side 168 of the electrode 46, thus causing most of the impedance measuring current to be injected into the tissue. Experimentation has shown that the use of some type of current reflection technique results in the percentage difference between the reference impedance and the assessment impedance to be between 50% and 100%.

There are several approaches to reflecting current into the tissue. One approach, as shown in FIG. 9b, is to use half-ring electrodes 46 positioned on the outside radius of curvature, such that when the catheter sheath 22 is positioned in the biological site the half-ring electrode is against the tissue. Another approach as shown in FIG. 9a, is to partially coat a full-ring electrode 46 with an electrically insulating but thermally conductive material 166. In yet another approach, as shown in FIG. 9c, an outer sheath comprised of an insulating material is used in conjunction with the catheter sheath 22. The distal segment 172 of the outer sheath is a half-pipe tube. The half-pipe tube segment 172 is positioned relative the electrodes 46 to shield the electrodes from the blood side 168.

Once it is determined that there is adequate electrode/tissue contact, ablation therapy of the tissue commences. During ablation, as depicted in FIGS. 10 through 12, the electrode device 44 and the backplates 16 are positioned proximal a biological site 174 undergoing ablation such that the biological site is interposed between the electrode device and the backplate. The band electrodes 46 (only one of which is indicated by a numeral 32 for clarity of illustration) of the electrode device 44 each receives power OUT1, OUT2, OUT3, OUT4 having a phase angle on LEAD 1 through LEAD 4. In one embodiment, every other electrode 46 receives the same phase angle. Therefore, the phase angle of electrode D equals the phase angle of electrode B and the phase angle of electrode C equals the phase angle of electrode A. The advantages of this arrangement are described below. In a preferred embodiment, the electrodes 46 are formed into a linear array as shown. In addition, a thermocouple thermal sensor 52 is located at each of the electrodes A, B, C, and D and uses the electrode power lead LEADS 1 through 4 as one of the sensor leads. The sensors provide temperature sensor signals 22 for receipt by the power control system 12.

In another embodiment, alternate electrodes 46 may be grouped together and each may receive the same power having the same phase angle and duty cycle. Another group or groups of electrodes 46 may be interspaced with the first group such that the electrodes of one group alternate with the electrodes of the other group or groups. Each electrode 46 in a particular group of electrodes has the same phase angle and duty cycle. For example, electrodes A and C may be connected to the same power while interspaced electrodes B and D may be connected to a different power output signal.

The use of individual power signals also provides the ability to disable any combination of electrodes 46 and thereby effectively change the length of the electrode device 24. For example, in one configuration of the present invention an electrode device 24 with twelve electrodes 46 receives twelve power signals from a twelve channel power control system 12. The electrodes 46 are 3 mm in length and are 4 mm apart. Accordingly, by disabling various electrodes, a virtual electrode of any length from 3 mm to 8 cm may be produced by the electrode device 24. In either arrangement the backplate 16 is maintained at the reference voltage level in regard to the voltage level of the power OUT1 through OUTn.

As previously described, by varying the phase angles between the power OUT1, OUT2 supplied to each electrode 46, a phase angle difference is established between adjacent band electrodes. This phase angle difference may be adjusted to control the voltage potential between adjacent band electrodes 46 and thus to control the flow of current through the biological site 174. The flow of current $I_{e\text{-}e}$ between adjacent band electrodes 46 is defined by:

$$I_{e\text{-}e} = \frac{2V\sin\left(\frac{\Delta\Phi}{2}\right)\sin(2\pi f t)}{Z_{e\text{-}e}} \quad \text{(Eq. 2)}$$

where:
 $\Delta\Phi$=phase angle difference between electrodes
 V=voltage amplitude of power
 $Z_{e\text{-}e}$=impedance between electrodes
 f=frequency in hertz
 t=time In addition to the current flow between the band electrodes 46 there is current flow between the band electrodes and the backplate 16. When the backplate 16 is set at the reference level, this current flow $I_{e\text{-}b}$ is defined by:

$$I_{e\text{-}b} = \frac{V\sin(2\pi f t)}{Z_{e\text{-}b}} \quad \text{(Eq. 3)}$$

where:
 $\Delta\Phi$=phase angle difference between electrodes
 V=voltage amplitude of power
 $Z_{e\text{-}b}$=impedance between electrode and backplate
 f=frequency in hertz
 t=time Assuming $Z_{e\text{-}b}$ and $Z_{e\text{-}e}$ are equal, the ratio of the current flowing between the band electrodes 46 $I_{e\text{-}e}$ to the current flowing between the band electrodes 46 and the backplate 16 $I_{e\text{-}b}$ is defined by:

$$\frac{I_{e\text{-}e}}{I_{e\text{-}b}} = 2\sin\left(\frac{\Delta\Phi}{2}\right) \quad \text{(Eq. 4)}$$

where:
 $\Delta\Phi$=phase angle difference between electrodes

FIGS. 10A through 12D illustrate various current flow patterns within a biological site. The depths and widths of the lesions depicted in FIGS. 10A through 12D are not necessarily to scale or in scalar proportion to each other but are provided for clarity in discerning the differences between the various power application techniques. When the phase difference between adjacent electrodes 46 is zero degrees, no current flows between the electrodes in accordance with Eq. 2 above, and the apparatus operates in a unipolar fashion with the current flowing to the backplate 16 as shown in FIGS. 10A through 10D. Substantially all current flows from the band electrodes 46 to the backplate 16 forming a series of relatively deep, acute lesions 176 along the length of the electrode device 24. As seen in the top view of FIG. 10B and the side view of FIG. 10D, the lesions are discrete. The lesions 176 are discontinuous in regard to each other.

Figure 11A:
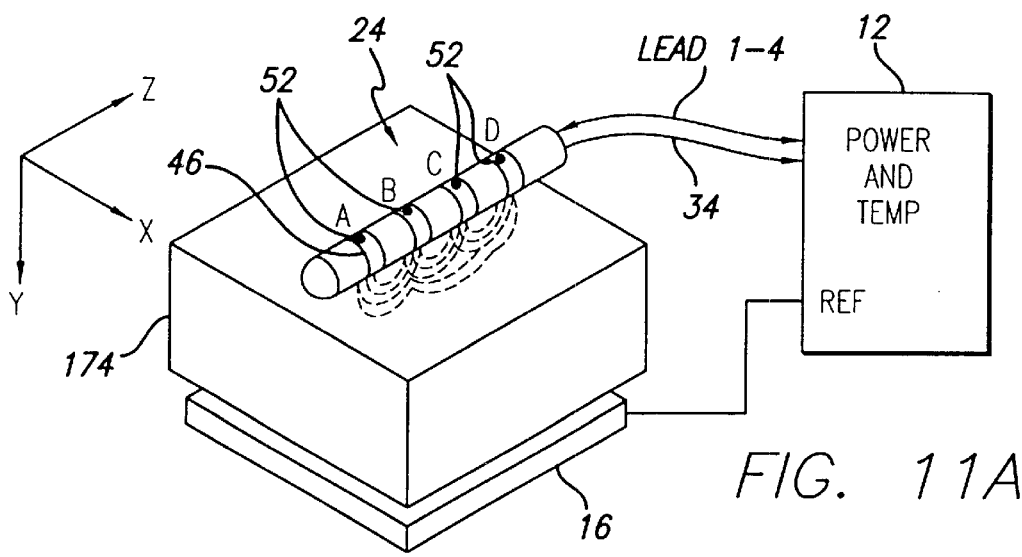
FIG. 11A is a three dimensional representation of an ablation apparatus having a linear array of band electrodes in contact with a biological site with a backplate at the opposite side of the biological site, in which the phase angle difference between adjacent electrodes is 180 degrees.
Figure 11B:
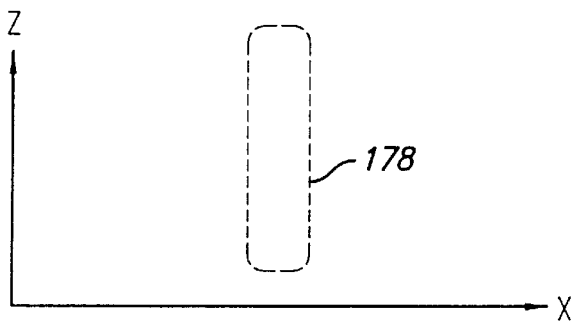
FIGS. 11B through 11D depict, along the x, y, and z axes shown, the continuity and depth of a lesion formed by the ablation apparatus of FIG. 10A showing that the apparatus acts as a bipolar device with no significant amount of current flowing to the backplate.
Figure 11C:
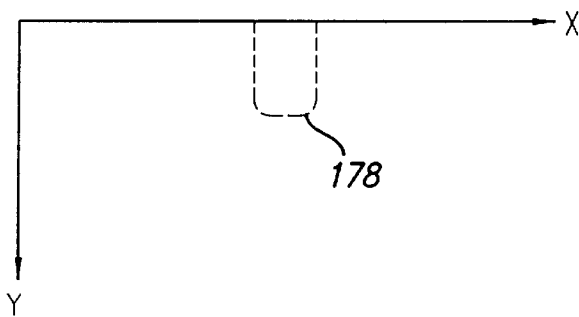
Figure 11D:
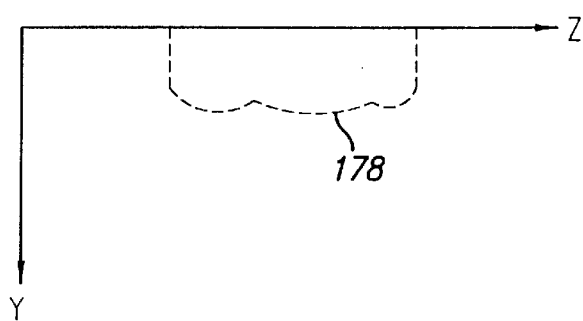

When the phase difference between adjacent electrodes 46 is 180 degrees the apparatus operates in both a unipolar and bipolar fashion and the current flow pattern is as shown in FIG. 11A. With this phase difference, approximately twice as much current flows between adjacent band electrodes 46 than flows from the band electrodes to the backplate 16. The resulting lesion 178 is shallow but is continuous along the length of the electrode device 44. The continuity and shallow depth of the lesion 178 are illustrated in FIGS. 11B through 11D. Nevertheless, the lesion depth is still greater than that created by prior bipolar ablation methods alone.

Figure 12A:
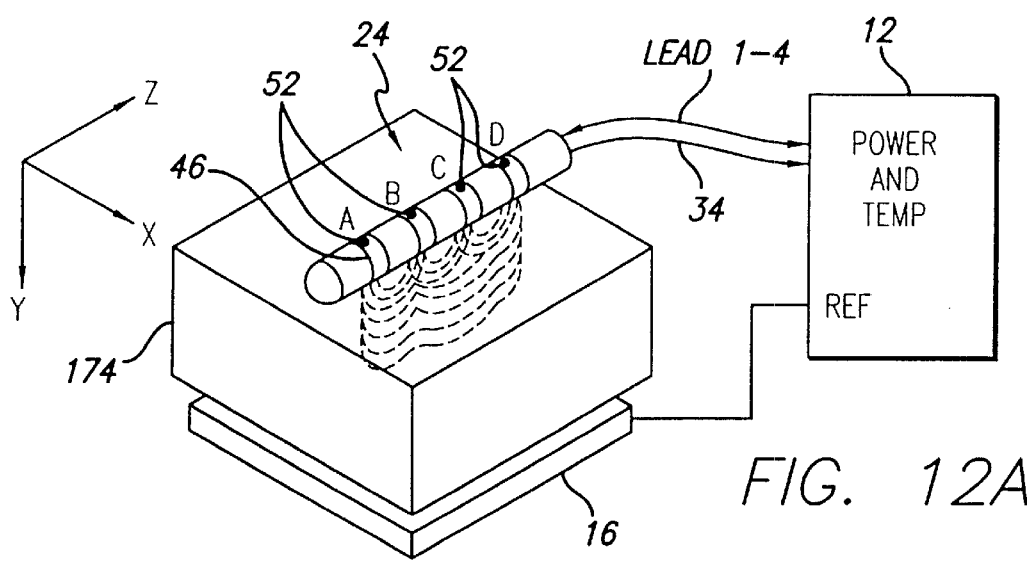
FIG. 12A is a three dimensional representation of an ablation apparatus having a linear array of band electrodes in contact with a biological site with a backplate at the opposite side of the biological site, in which the phase difference between adjacent electrodes is approximately 90 degrees.
Figure 12B:
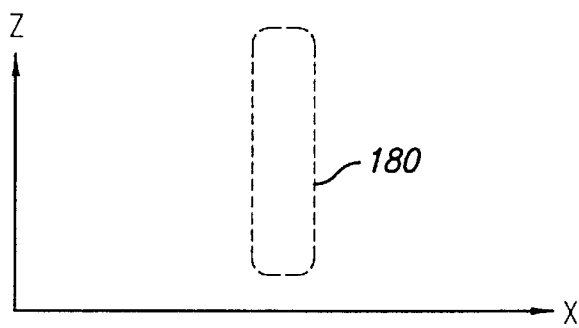
FIGS. 12B through 12D depict, along the x, y, and z axes shown, the continuity and depth of a lesion formed by the ablation apparatus of FIG. 11A showing the greater depth of lesion resulting from the phase angle difference.
Figure 12C:
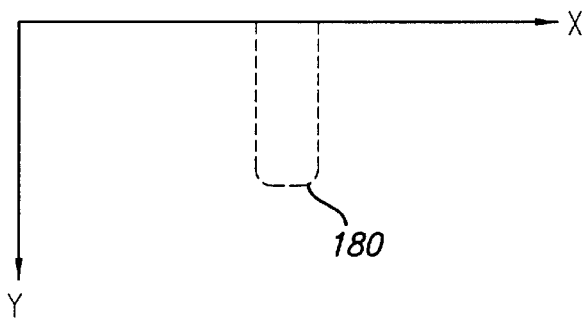
Figure 12D:
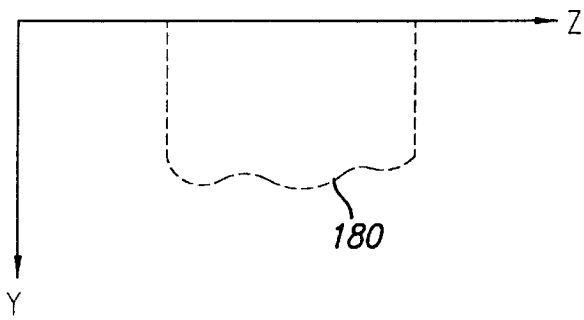

When the phase difference between adjacent electrodes 46 is set within the range of a value greater than zero to less than 180 degrees, the current flow varies from a deep, discontinuous unipolar pattern to a more continuous, shallow bipolar pattern. For example, when the phase difference between adjacent electrodes 46 is around 90 degrees, the current flows as shown in FIG. 12A. With this phase difference, current flows between adjacent band electrodes 46 as well as between the band electrodes and the backplate 16. Accordingly, a lesion which is both deep and continuous along the length of the electrode device 24 is produced. The continuity and depth of the lesion 180 is illustrated in FIGS. 12B through 12D. In one embodiment of FIG. 12A, adjacent electrodes alternated in phase but were provided with power in groups. Electrodes A and C were provided with power at a first phase angle and electrodes B and D were provided with power at a second phase angle, different from the first.

Thus, the phase angle of the power may be adjusted in order to produce a lesion having different depth and continuity characteristics. In selecting the phase angle difference necessary to produce a continuous lesion having the greatest possible depth, other elements of the electrode device 24 are considered. For example, the width of the band electrodes 46 and the spacing between the electrodes are factors in selecting an optimum phase angle. In a preferred embodiment of the present invention, as pointed out above, the width of the band electrodes is 3 mm, the spacing between the electrodes is 4 mm and the electrodes receive power which establish a phase difference of 132 degrees between adjacent electrodes. With this configuration a long continuous lesion having a length of between approximately 3 mm and 8 cm and a depth of 5 mm or greater was produced depending on the number of electrodes energized, the duty cycle employed, and the duration of power application.

In another embodiment of the invention, during the application of ablation power to the electrodes, the electrical activity of the tissue undergoing ablation therapy is captured and sent to an external device for analysis. Biological tissue, particularly heart tissue is electrically active and thus serves as a source of electrical energy. During ablation, the electrode in contact with the tissue not only delivers power to the tissue, it also senses the electrical signals passing through the tissue and feeds back these signals to the ECG filter system 36 (FIG. 4). Thus at the input to the ECG filter 128 (FIG. 6F) is a combination signal comprising both the ablation power signal and the tissue feedback signal. The present invention makes the tissue feedback signal available for immediate analysis by an ECG amplifier/recorder by filtering the high-frequency ablation power component from the combination signal. This filtering process continues throughout the ablation procedure thus allowing for ECG analysis to occur during ablation therapy. When ablation power is not being applied trough an electrode, that electrode still provides a tissue feedback signal to the ECG filter associated with the electrode. As there is no ablation power signal to filter, the tissue feedback signal passes through the ECG filter and is available for analysis by the ECG amplifier/recorder.

It will be apparent from the foregoing that while particular forms of the invention have been illustrated and described, various modifications can be made without departing from the spirit and scope of the invention. Accordingly, it is not intended that the invention be limited, except as by the appended claims.

What is claimed is:

1. A method of assessing the adequacy of contact between an ablation electrode carried by an electrode device and biological tissue within a moving biological organ having biological fluid therein, said method comprising the steps of:
    positioning the ablation electrode in the biological fluid;
    positioning a reference electrode a distance from a first electrode and the biological tissue;
    obtaining a reference impedance value by measuring the impedance between the ablation electrode and the reference electrode, wherein the reference impedance value is the average of a plurality of reference impedance values obtained during a given time period sufficient to include a plurality of organ movements;
    moving the ablation electrode to a position proximal the biological tissue;
    obtaining an assessment impedance value by measuring the impedance between the ablation electrode and the reference electrode, wherein the assessment impedance value is the average of a plurality of assessment impedance values obtained during a given time period sufficient to include a plurality of organ movements;
    analyzing the assessment impedance and the reference impedance; and
    indicating the state of electrode/tissue contact.

2. The method of claim 1 wherein the step of analyzing the assessment impedance and the reference impedance comprises the step of calculating the percentage difference between the two and the step of indicating the state of electrode/tissue contact comprises the steps of:
    when the percentage difference is at least approximately 10%, indicating substantially complete electrode/tissue contact;
    when the percentage difference is in the approximate range between 5% and 10%, indicating partial electrode/tissue contact; and
    when the percentage difference is less than approximately 5%, indicating no electrode/tissue contact.

3. The method of claim 1 wherein the reference electrode is positioned in the biological fluid.

4. The method of claim 1 wherein the reference electrode is positioned exterior to the biological organ.

5. The method of claim 1 wherein the electrode device carries a plurality of electrodes one of which comprises the ablation electrode and another of which comprises the reference electrode.

6. The method of claim 1 wherein the organ is a heart and the reference impedance and the assessment impedance are obtained using a drive signal having a frequency above that which induces pacing of the heart and a voltage level below that which induces pacing of the heart.

7. The method of claim 1 further comprising the step of, prior to obtaining an assessment impedance value, positioning an electrical insulator relative the ablation electrode so that when the ablation electrode is proximal the biological tissue the electrode is interposed between the electrical insulator and the tissue.

8. The method of claim 7 wherein the ablation electrode comprises a ring electrode and the electrical insulator comprises a dielectric material having normal thermal conductivity adhered to a portion of the ring electrode.

9. The method of claim 7 wherein the ablation electrode comprises a ring electrode and the electrical insulator comprises a half-pipe sheath surrounding a portion of the ring electrode.

10. The method of claim 9 wherein the ablation electrode comprises a half-ring electrode and the electrical insulator comprises a catheter sheath onto which the half-ring electrode is mounted.

11. A method of assessing the adequacy of contact between a plurality of ablation electrodes carried by an electrode device and biological tissue within a biological organ having biological fluid therein, said method comprising the steps of:
    obtaining a reference impedance value by:
        positioning the plurality of ablation electrodes in the biological fluid;
        positioning a first reference electrode a distance from the plurality of ablation electrodes and the biological tissue;
        measuring the impedance between at least one of the ablation electrodes and the reference electrode;
    moving the plurality of ablation electrodes to a position proximal the biological tissue;

for each ablation electrode:
obtaining an assessment impedance value by positioning a second reference electrode a distance from the ablation electrode and the biological tissue and measuring the impedance between the ablation electrode and the reference electrode;
analyzing the assessment impedance and the reference impedance; and
indicating the state of electrode/tissue contact.

12. The method of claim 11 wherein the step of analyzing the assessment impedance and the reference impedance comprises the step of calculating the percentage difference between the two and the step of indicating the state of electrode/tissue contact comprises the steps of:
when the percentage difference is at least approximately 10%, indicating substantially complete electrode/tissue contact;
when the percentage difference is in the approximate range between 5% and 10%, indicating partial electrode/tissue contact; and
when the percentage difference is less than approximately 5%, indicating no electrode/tissue contact.

13. The method of claim 11 wherein the second reference electrode comprises one of the plurality of ablation electrodes.

14. The method of claim 11 wherein the second reference electrode comprises a backplate.

15. A method of assessing the adequacy of contact between a plurality of ablation electrodes carried by an electrode device and biological tissue within a biological organ having biological fluid therein, said method comprising the steps of:
obtaining a reference impedance value by:
positioning the plurality of ablation electrodes in the biological fluid;
positioning a first reference electrode a distance from the plurality of ablation electrodes and the biological tissue;
measuring the impedance between at least one of the ablation electrodes and the reference electrode;
moving the plurality of ablation electrodes to a position proximal the biological tissue;
obtaining an assessment impedance value by measuring the impedance between selected pairs of ablation electrodes;
analyzing the assessment impedance and the reference impedance; and
indicating the state of electrode/tissue contact.

16. The method of claim 15 wherein the step of analyzing the assessment impedance and the reference impedance comprises the step of calculating the percentage difference between the two and the step of indicating the likelihood of electrode/tissue contact comprises the steps of:
when the percentage difference is at least approximately 10%, indicating substantially complete electrode/tissue contact;
when the percentage difference is in the approximate range between 5% and 10%, indicating partial electrode/tissue contact; and
when the percentage difference is less than approximately 5%, indicating no electrode/tissue contact.

17. The method of claim 15 wherein the ablation electrodes are arranged in a linear array and the pairs of ablation electrodes comprise adjacent electrodes.

18. A method of assessing the adequacy of contact between an ablation electrode and biological tissue within a moving biological organ having biological fluid therein, said method comprising the steps of:
positioning the ablation electrode proximal the biological tissue;
positioning a reference electrode a distance from the ablation electrode;
applying a signal to the ablation electrode during a time period sufficient to include several movements of the organ;
obtaining a sequence of impedance values by periodically measuring the impedance between the ablation electrode and the reference electrode during the time period; and
monitoring the sequence of impedance values for variations indicative of electrode/tissue contact.

19. The method of claim 18 wherein the step of monitoring the sequence of impedance values for variations indicative of electrode/tissue contact comprises the steps of:
obtaining an average impedance value based on a plurality of the impedance values;
calculating the standard deviation of the impedance values relative the average impedance;
calculating a deviation percentage;
when the deviation percentage is at least approximately 2%, indicating substantially complete electrode/tissue contact;
when the deviation percentage is in the approximate range between 1% and 2%, indicating partial electrode/tissue contact; and
when the deviation percentage is less than approximately 1%, indicating no electrode/tissue contact.

20. A method of assessing the adequacy of contact between an ablation electrode and biological tissue within a biological organ having biological fluid therein, said method comprising the steps of:
positioning the ablation electrode proximal the biological tissue;
positioning a reference electrode a distance from the ablation electrode;
measuring the impedance between the ablation electrode and the reference electrode at a first frequency;
measuring the impedance between the ablation electrode and the reference electrode at a second frequency;
analyzing the first-frequency impedance and the second-frequency impedance; and
indicating the state of electrode/tissue contact.

21. The method of claim 20 wherein the step of analyzing the first-frequency impedance and the second-frequency impedance comprises the step of calculating the percentage difference between the two impedances and the step of indicating the state of electrode/tissue contact comprises the steps of:
when the percentage difference is at least approximately 10%, indicating substantially complete electrode/tissue contact;
when the percentage difference is in the approximate range between 5% and 10%, indicating partial electrode/tissue contact; and
when the percentage difference is less than approximately 5%, indicating no electrode/tissue contact.

22. The method of claim 20 wherein the step of analyzing the first-frequency impedance and the second-frequency impedance comprises the steps of calculating the ratio of the two impedances and comparing the ratio to a known value, and the step of indicating the state of electrode/tissue contact comprises the steps of:

when the ratio is approximately equal to the known value, indicating no electrode/tissue contact;

when the ratio deviates from the known value by an amount in the approximate range between ±0.1 to ±0.15, indicating at least partial electrode/tissue contact; and when the ratio deviates from the known value by an amount approximately greater than ±0.15, indicating substantially complete electrode/tissue contact.

23. The method of claim 20 wherein there is at least a two fold difference between the first frequency and second frequency.

24. The method of claim 23 wherein one of the frequencies is a low-frequency just above that which induces pacing of the heart and the other of the frequencies is a greater than the low frequency.

25. The method of claim 20 wherein the first-frequency impedance is the average of a plurality of impedances measured during a first time period and the second-frequency impedance is the average of a plurality of impedances measured during a second time period.

26. A method of assessing the adequacy of contact between an ablation electrode carried by an electrode device and biological tissue within a biological organ having biological fluid therein, said method comprising the steps of:

positioning the ablation electrode in the biological fluid;

positioning a reference electrode a distance from the ablation electrode;

measuring the impedance between the ablation electrode and the reference electrode at a first frequency;

measuring the impedance between the ablation electrode and the reference electrode at a second frequency;

obtaining a base-line ratio by calculating the ratio of the first-frequency impedance and the second-frequency impedance;

positioning the ablation electrode proximal the biological tissue;

positioning the reference electrode a distance from the ablation electrode;

measuring the impedance between the ablation electrode and the reference electrode at the first frequency;

measuring the impedance between the ablation electrode and the reference electrode at the second frequency;

obtaining a contact assessment ratio by calculating the ratio of the first-frequency impedance and the second-frequency impedance;

analyzing the base-line ratio and the contact-assessment ratio; and indicating the state of electrode/tissue contact.

27. The method of claim 26 wherein the step of analyzing the base-line ratio and the contact-assessment ratio comprises the step of comparing the ratios and the step of indicating the state of electrode/tissue contact comprises the steps of:

when the assessment ratio is approximately equal to the base-line ratio, indicating no electrode/tissue contact;

when the assessment ratio deviates from the base-line ratio by a value in the approximate range between ±0.1 to ±0.15, indicating at least partial electrode/tissue contact; and when the assessment ratio deviates from the base-line ratio by an amount approximately greater than ±0.15, indicating substantially complete electrode/tissue contact.

28. An apparatus for assessing the adequacy of contact between an ablation electrode and biological tissue within a moving biological organ having biological fluid therein, said apparatus comprising:

an electrode device carrying the ablation electrode;

a signal generating device providing as output a drive signal to the ablation electrode and a reference potential;

a reference electrode spaced from the ablation electrode and responsive to the reference potential;

an impedance measurement device configured to:

provide a reference impedance indicative of the impedance between the ablation electrode and the reference electrode when the ablation electrode is positioned in the biological fluid, wherein the reference impedance value is the average of a plurality of reference impedance values obtained during a given time period sufficient to include a plurality of organ movements; and provide an assessment impedance indicative of the impedance between the ablation electrode and the reference electrode when the ablation electrode is positioned proximal the biological tissue wherein the assessment impedance value is the average of a plurality of assessment impedance values obtained during a given time period sufficient to include a plurality of organ movements; and a processor responsive to the reference and assessment impedance signals configured to analyze the impedance signals and indicate the state of electrode/tissue contact.

29. The apparatus of claim 28 wherein the processor comprises:

a calculator configured to determine the percentage difference between the reference impedance and the assessment impedance; and a comparator configured to compare the percentage difference to a plurality of predetermined contact assessment criteria and provide an indication result, the criteria and results comprising, for a percentage difference at least approximately 10%, indicating substantially complete electrode/tissue contact, for a percentage difference in the approximate range between 5% and 10%, indicating partial electrode/tissue contact, and for a percentage difference less than approximately 5%, indicating no electrode/tissue contact.

30. The apparatus of claim 28 wherein the electrode device carries a plurality of electrodes one of which comprises the ablation electrode and another of which comprises the reference electrode.

31. The apparatus of claim 28 wherein the amplitude of the drive signal is limited to a level below that which induces pacing of a heart.

32. The apparatus of claim 31 wherein the voltage level is between 20 millivolts and 200 millivolts.

33. The apparatus of claim 32 wherein the voltage level is approximately 50 millivolts.

34. The apparatus of claim 28 wherein the electrode device comprises an electrical insulator positioned relative the ablation electrode so that when the ablation electrode is proximal the biological tissue the electrode is interposed between the electrical insulator and the tissue.

35. The apparatus of claim 34 wherein the ablation electrode comprises a ring electrode and the electrical insulator comprises a dielectric material having normal thermal conductivity adhered to a portion of the ring electrode.

36. The apparatus of claim 34 wherein the ablation electrode comprises a ring electrode and the electrical insulator comprises a half-pipe sheath surrounding a portion of the ring electrode.

37. The apparatus of claim 34 wherein the ablation electrode comprises a half-ring electrode and the electrical insulator comprises a catheter sheath onto which the half-ring electrode is mounted.

38. An apparatus for assessing the adequacy of contact between an ablation electrode and biological tissue within a moving biological organ having biological fluid therein, said apparatus comprising:

an electrode device carrying the ablation electrode;

a signal generating device providing as output a drive signal to the ablation electrode and a reference signal;

a reference electrode spaced from the ablation electrode and responsive to the reference signal;

an impedance measurement device configured to provide a sequence of assessment impedance values indicative of the impedance between the ablation electrode and the reference electrode; and a processor responsive to the sequence of assessment impedance signals configured to monitor the sequence of impedance values for variations indicative of electrode/tissue contact.

39. The apparatus of claim 38 wherein the processor comprises:

a calculator configured to determine an average impedance value based on a plurality of the impedance values, calculate the standard deviation of the impedance values relative the average impedance and calculate a deviation percentage; and a comparator configured to compare the deviation percentage to a plurality of predetermined contact assessment criteria and provide an indication result, the criteria and results comprising, for a deviation percentage at least approximately 2%, indicating substantially complete electrode/tissue contact, for a deviation percentage in the approximate range between 1% and 2%, indicating partial electrode/tissue contact; and for a standard deviation percentage less than approximately 1%, indicating no electrode/tissue contact.

40. An apparatus for assessing the adequacy of contact between an ablation electrode carried by an electrode device and biological tissue within a biological organ having biological fluid therein, said apparatus comprising:

a signal generating device providing as output a reference signal and for a first time period, a first drive signal to the ablation electrode, the first drive signal having a first amplitude and first frequency, the signal generating device also providing as output for a second time period, a second drive signal to the ablation electrode, the second drive signal having a second amplitude and a second frequency;

a reference electrode spaced from a first electrode and responsive to the reference signal;

an impedance measurement device producing as output a first assessment impedance signal indicative of the impedance between the ablation electrode and reference electrode during the first time period and a second assessment impedance signal indicative of the impedance between the first and second electrodes during the second time period; and a processor responsive to the first and second assessment impedance signals configured to compare the impedances to a predetermined value indicative of electrode/tissue contact.

41. The apparatus of claim 40 wherein the processor comprises:

a calculator configured to determine the percentage difference between the first-frequency impedance and the second-frequency impedance; and a comparator configured to compare the percentage difference to a plurality of predetermined contact assessment criteria and provide an indication result, the criteria and results comprising, for a percentage difference at least approximately 10%, indicating substantially complete electrode/tissue contact, for a percentage difference in the approximate range between 5% and 10%, indicating partial electrode/tissue contact, and for a percentage difference less than approximately 5%, indicating no electrode/tissue contact.

42. The apparatus of claim 40 wherein the processor comprises:

a calculator configured to determine the ratio of the first-frequency impedance and the second-frequency impedance; and a comparator configured to compare the ratio to a plurality of predetermined contact assessment criteria and provide an indication result, the criteria and results comprising, for a ratio of approximately 1, indicating no electrode/tissue contact and for a ratio that deviates significantly from 1, indicating electrode/tissue contact.

43. A method of providing ablation energy to biological tissue through an electrode device having at least one electrode while monitoring the electrical activity of the tissue, said method comprising the steps of:

positioning the at least one electrode proximal the tissue;

applying ablation power to the at least one electrode through a first lead, the ablation power comprising a high frequency component;

receiving, from the electrode and through the first lead, a feedback signal indicative of the electrical activity in the tissue;

filtering the feedback signal to remove any high frequency components; and providing the filtered feedback signal to an instrument through a second lead.

44. The method of claim 43 wherein the ablation power comprises an RF component and the filter filters the RF component from the feedback signal.

45. The method of claim 44 wherein the RF component has a frequency of approximately 500 kHz.

46. The method of claim 43 wherein the filtered feedback signal comprises an electrocardiogram signal having a frequency less that 250 Hz and the instrument is an electrocardiogram amplifier/recorder.

47. An apparatus for providing ablation power to biological tissue through an electrode device having at least one electrode positioned proximal the tissue, said apparatus comprising:

a generator producing ablation power having a high-frequency component;

a high-frequency filter;

a first lead presenting the ablation power to the at least one electrode and the filter, the first lead further presenting a feedback signal from the electrode to the filter; and a second lead presenting a filter output to an instrument.

48. The apparatus of claim 47 wherein the ablation power comprises an RF component and the high-frequency filter filters the RF component.

49. The apparatus of claim 48 wherein the RF component has a frequency of approximately 500 kHz.

50. The apparatus of claim 47 wherein the filter output comprises an electrocardiogram signal having a frequency less that 250 Hz and the instrument comprises an electrocardiogram amplifier/recorder.

51. An apparatus comprising:

a generator producing a plurality of ablation power signals, each having a high frequency component;

a plurality of high-frequency filters;

an electrode device having a plurality of electrodes;

a plurality of first leads, each presenting one of the ablation power signals to one of the electrodes and one of the filters, the first lead further presenting a feedback signal from the electrode to the filter; and a plurality of second leads, each presenting a filter output to an instrument.

* * * * *